US008226944B2

(12) United States Patent
Song et al.

(10) Patent No.: US 8,226,944 B2
(45) Date of Patent: Jul. 24, 2012

(54) COMPOSITION FOR TREATING VIRUS INFECTION DISEASE COMPRISING JAB1

(75) Inventors: Jaewhan Song, Seongnam-si (KR); Wonkyung Oh, Gwangju (KR); Young Hoon Sung, Suwon-si (KR); Sung Ryul Lee, Yongin-si (KR); Han-Woong Lee, Seongnam-si (KR); Suhk Neung Pyo, Seoul (KR); Joo-Sung Yang, Seoul (KR)

(73) Assignee: Sungkyunkwan University, Seoul (KR)

( * ) Notice: Subject to any disclaimer, the term of this patent is extended or adjusted under 35 U.S.C. 154(b) by 0 days.

(21) Appl. No.: 12/909,443

(22) Filed: Oct. 21, 2010

(65) Prior Publication Data

US 2011/0092414 A1 Apr. 21, 2011

Related U.S. Application Data

(62) Division of application No. 10/531,543, filed as application No. PCT/KR2004/002190 on Aug. 31, 2004, now abandoned.

(51) Int. Cl.
*A61K 39/395* (2006.01)
*A61K 39/42* (2006.01)
(52) U.S. Cl. .................................. 424/130.1; 424/159.1
(58) Field of Classification Search ................ 424/131.1, 424/147.1, 159.1
See application file for complete search history.

(56) References Cited

U.S. PATENT DOCUMENTS 5,948,883 A 9/1999 Yoshida et al. ............... 530/300

OTHER PUBLICATIONS

Hallstrom et al., Jab1 is a specificity factor for E2F1-induced apoptosis Genes & Development 20:613-623.*
Shackleford and Claret JAB1/CSN5: a new player in cell cycle control and cancer Cell Division 2010, 5:26 pp. 1-14.*
Ho et al., Hsp70 functions as a negative regulator of West Nile virus capsid protein through direct interaction.Biochemical and Biophysical Research Communications 347 (2006) 994-1000.*
Lee et al., Jab1 as a Mediator of Nuclear Export and Cytoplasmic Degradation of p53 Mol. Cells, vol. 22, No. 2, pp. 133-140.*
Rudinger, J., "Characteristics of the amino acids as components of a peptide hormone sequence",in Peptide Hormones, University Park Press: Baltimore, MD, pp. 1-7, 1976.*
Kimchi-Sarfaty Cet al., A "silent" polymorphism in the MDR1 gene changes substrate specificity.Science. Jan. 26, 2007;315(5811):525-8.*
Skolnick et al. From genes to protein structure and function: novel applications of computational approaches in the genomic era; (Trends Biotechnol. Jan. 2000;18(1):34-9.*
Bowie, et al. (Science, 247: 1306-10, 1990).*
Oh et al., Jab1 Mediates Cytoplasmic Localization and Degradation of West Nile Virus Capsid Protein The Journal of Biological Chemistry vol. 281, No. 40, pp. 30166-30174, Oct. 6, 2006.*
Seeger, et al., "A Novel Protein Complex Involved in Signal Transduction Possessing Similarities to 26S Proteasome Subunits," The FASEB Journal, Apr. 1998, vol. 12, pp. 469-478.
Sharma, et al., "Triggering the Interferon Antiviral Response Through an IKK-Related Pathway," Science, May 2003, vol. 300, pp. 1148-1151.
Park, et al., "Hepatitis C Virus NS5A Protein Modulates c-Jun N-terminal Kinase through Interaction with Tumor Necrosis Factor Receptor-associated Factor 2," The Journal of Biological Chemistry, Aug. 2003, vol. 278, pp. 30711-30718.
Pletnev, et al., "Nucleotide Sequence of the Genome and Complete Amino Acid Sequence of the Polyprotein of Tick-Borne Encephalitis Virus," Virology, 1990, vol. 174, pp. 250-263.
Chamovitz, et al., "JAB1/CSN5 and the COP9 Signalosome," EMBO Reports, 2001, vol. 2, pp. 96-101.
Kouvaraki, et al., "Jun Activation Domain-binding Protein 1 Expression in Breast Cancer Inversely Correlates with the Cell Cycle Inhibitor p27Kip11," Cancer Research, Jun. 2003, vol. 63, pp. 2977-2981.
Tsutsumi, et al., "Alteration of Intrahepatic Cytokine Expression and AP-1 Activation in Transgenic Mice Expressing Hepatitis C Virus Core Protein," Virology, 2002, vol. 304, pp. 415-424.
Soo, et al., "Expression of a Full-Length Hepatitis C Virus cDNA Up-Regulates the Expression of CC Chemokines MCP-1 and RANTES," Virology, 2002, vol. 303, pp. 253-277.
Anninger et al., "Visual Loss with West Nile Virus Infection: A Wider Spectrum of a "New" Disease," vol. 38, pp. e55-56, Dept. of Ophthalmology, Ohio State University Medical Center (2004).
Agrawal et al., "Human Immunoglobulin as a Treatment for West Nile Virus Infection," vol. 188, pp. 1-4, The Journal of Infections Diseases (2003).
Watt et al., "Acute Undifferentiated Fever Caused by Infection with Japanese Encephalitis Virus," pp. 704-706, Department of Retrovirology, Armed Forces Research Institute of Medical Sciences, (2003).
Morrey et al., "Identification of active antiviral compounds against a New York isolate of West Nile virus," pp. 107-116, Antiviral Research 55 (2002).
Caballero et al., "Interaction and Colocalization of PGP9.5 with JAB1 and p27Kip1," vol. 21, pp. 3003-3010, Oncogene (2002).
Yang et al., "Induction of Inflamation by *West Nile Virus* Capsid through the Caspase-9 Apoptotic Pathway," vol. 8, No. 12, pp. 1379-1384, Emerging Infectuous Diseases, Dec. 2002.
"Efficacy of Interferon Alpha-2b and Ribavirin against *West Nile Virus* In Vitro," vol. 8, No. 1, pp. 107-108, Emerging Infectuous Diseases, Jan. 2002.

(Continued)

*Primary Examiner* — Maria Leavitt
(74) *Attorney, Agent, or Firm* — Casimir Jones SC

(57) ABSTRACT

Disclosed is a composition for treating or preventing a viral infection or associated disease comprising a Jab1 protein, a nucleic acid having a nucleotide sequence coding for a Jab1 protein or a recombinant virus expressing a Jab1 protein.

3 Claims, 18 Drawing Sheets

FIG. 9

COMPOSITION FOR TREATING VIRUS INFECTION DISEASE COMPRISING JAB1

CROSS-REFERENCE TO RELATED APPLICATIONS

The present application is a divisional of U.S. Ser. No. 10/531,543, now abandoned, filed Oct. 28, 2005, which is a National Stage Filing of, and claims priority to, PCT Patent Application No. PCT/KR/2004/002190, filed Aug. 31, 2004. U.S. Ser. No. 10/531,543 and PCT/KR/2004/002190 are incorporated herein by reference in their entireties.

BACKGROUND OF THE INVENTION

1. Field of the Invention

The present invention relates, in general, to a composition for treating a viral infection comprising Jab1. More particularly, the present invention relates to a composition for treating or preventing a viral infection comprising a Jab1 (Jun-activation binding protein 1) protein, a nucleic acid having a nucleotide sequence coding for a Jab1 protein or a recombinant virus expressing a Jab1 protein.

2. Description of the Related Art

Flavivirus and pestivirus belong to the Flaviviridae family which possesses a single-stranded positive sense RNA genome and causes various diseases in vertebrate hosts. West Nile virus (WNV) (Burt et al., Emerg Infect Dis., 8(8):820-826, 2002; Asnis et al., Clin Imfect Dis 30(3): 413-418, 2000) causes diseases including fever, rash, arthralgia and myalgia when infecting susceptible hosts. Apoptosis in wild-type WNV-infected brain cells is induced in a Bax-dependent manner (Parquet et al., FEBS Lett., 500(1-2):17-24. 2001), and the apoptosis is induced by the capsid protein of WNV through the mitochondrial/caspase-9 pathway (Yang et al., Emerg Infect Dis., 8(12):1379-1384, 2002). However, the intracellular pathological mechanism of West Nile virus infection has not been completely understood.

Immunoglobulins and antiviral agents such as interferon alpha-2b and ribavirin were conventionally used for preventing and treating West Nile virus infection (Agrawal and Petersen., J Infect Dis, 188(1):1-4, 2003; Morrey et al., Antiviral Res., 55(1):107-116, 2002; Anderson et al., Emerg Infect Dis., 8(1):107-108, 2002), but they have low therapeutic effects. At present, there is no effective drug for treating or preventing West Nile virus infection. Thus, there is a need for the development of such effective drugs.

On the other hand, Jab1 (Jun-activation binding protein 1) was initially known as a coactivator of AP-1 (Jun/Fos proto-oncogene) protein and has the following, various functions. Jab1 is a component (CSN5) of the COP9 signalosome (CSN) (Wei et al., Annu Rev Cell Dev Biol., 19:261-286, 2003), and Jab1/CSN5 exists in a wide spectrum of organisms, ranging from yeasts to plants and animals. Overexpression of Jab1 causes the translocation of cyclin dependent kinase inhibitor p27/Kip1 from the nucleus to the cytoplasm, accelerates the Ub-26S proteasome-dependent degradation, and participates in the G1-S transition of the cell cycle, mediated by p27/Kip1 (Tomoda et al., Nature, 398(6723):160-165, 1999). In addition, Jab1 involves the nuclear translocation of PGP9.5 that is overexpressed in primary lung cancer cells (Caballero et al., Oncogene, 21(19):3003-3010, 2002). Jab1 interacts with p53, Smad4 and lutropin/choriogonadotropin receptor and stimulates degradation of these proteins (Bech-Otschir et al., EMBO J., 20(6):1630-1639, 2001; Li et al. J Biol Chem., 275(18):13386-13393, 2000; Wan et al., EMBO J., 3(2):171-176, 2002). Taken together, Jab1 translocates proteins from the nucleus to the cytoplasm by interaction with intracellular proteins and thus stimulates protein degradation in a proteasome-dependent manner.

However, there is no report for interaction between Jab1 and viral proteins upon flavivirus infection.

Based on this background, the present inventors identified Jab1 as a protein interacting with the capsid protein of flavivirus, and found that Jab1 inhibits apotosis by accelerating degradation of the capsid protein and that Jab1 is useful for treating or preventing a viral infection, thereby leading to the present invention.

SUMMARY OF THE INVENTION

It is therefore an object of the present invention to provide a composition for treating or preventing a flavivirus or pestivirus infection, which comprises a Jab1 (Jun-activation binding protein 1) protein.

It is another object of the present invention to provide a composition for treating or preventing a flavivirus or pestivirus infection, which comprises a nucleic acid having a nucleotide sequence coding for a Jab1 protein.

It is a further object of the present invention to provide a composition for treating or preventing a flavivirus or pestivirus infection, which comprises a recombinant virus expressing a Jab1 protein.

It is yet another object of the present invention to provide a method of treating or preventing a flavivirus or pestivirus infection, which is based on administering a pharmaceutically effective amount of a Jab1 protein to a subject requiring treatment or prevention of a viral infection.

It is still another object of the present invention to provide a method of treating or preventing a flavivirus or pestivirus infection, which is based on administering a pharmaceutically effective amount of a nucleic acid having a nucleotide sequence coding for a Jab1 protein to a subject requiring treatment or prevention of a viral infection.

It is still another object of the present invention to provide a method of treating or preventing a flavivirus or pestivirus infection, which is based on administering a pharmaceutically effective amount of a recombinant virus expressing a Jab1 protein to a subject requiring treatment or prevention of a viral infection.

It is still another object of the present invention to provide a method of assaying a substance stimulating expression of a Jab1 protein.

BRIEF DESCRIPTION OF THE DRAWINGS

The above and other objects, features and other advantages of the present invention will be more clearly understood from the following detailed description taken in conjunction with the accompanying drawings, in which:

FIG. 8 shows that co-expression of Jab 1 and WNV-Cp leads to a decrease in caspase activity, wherein FIG. 8A shows a graph for the results of measuring caspase activity to each protein, and FIG. 8B refers to the western blotting results for the expression of protein;

FIG. 9 shows the results of Western blotting, displaying that degradation of WNV-Cp by Jab1 is remarkably suppressed in the presence of a 26S proteasome inhibitor LLnL;

FIG. 17B shows the data for pShuttle-Jab1 and pShuttle-Cp. And, FIG. 17C represents western blotting data for Jab1 isolated by PacI enzyme after transformation.

DETAILED DESCRIPTION OF THE INVENTION

Figure 1:
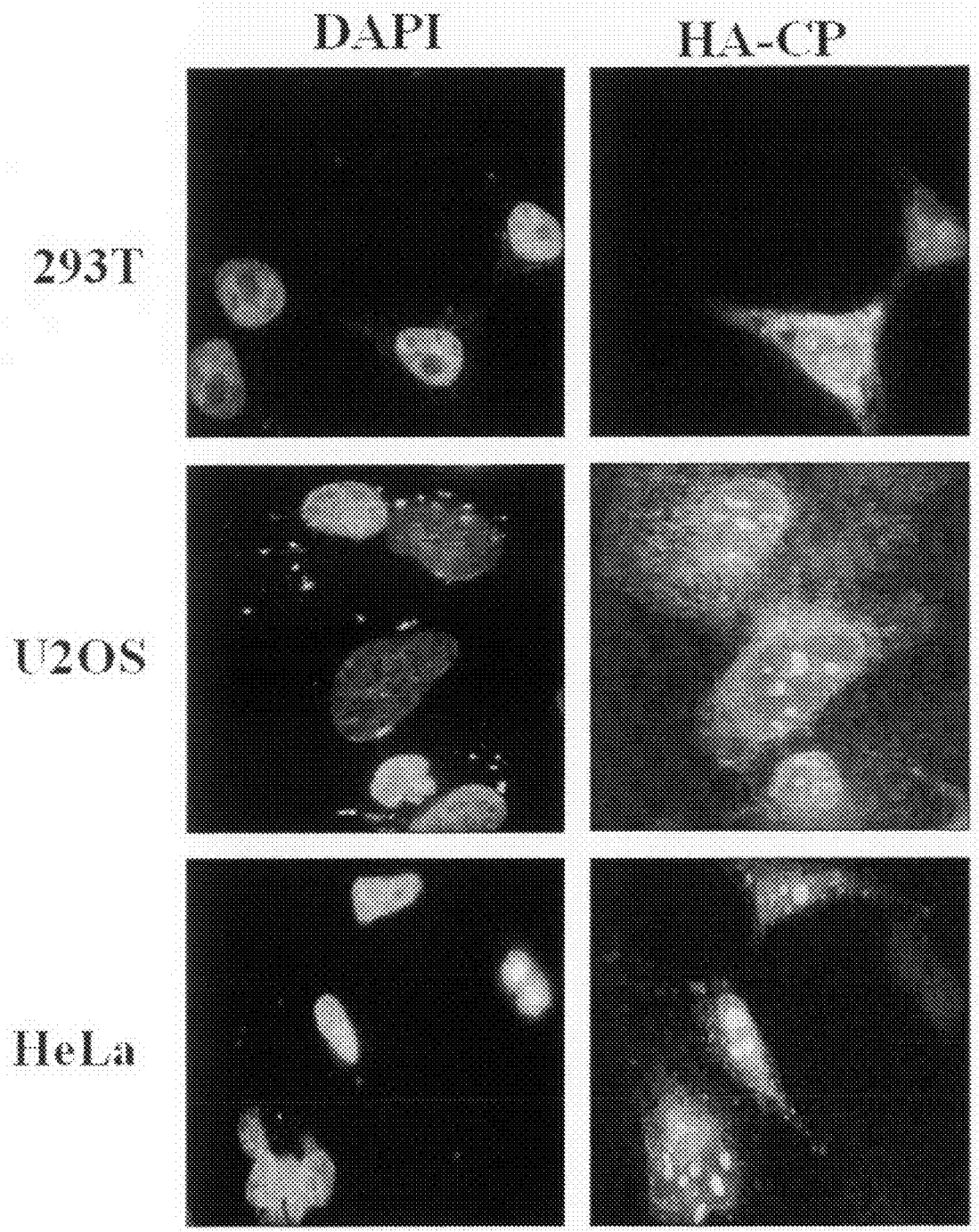
FIG. 1 shows the results of immunofluorescence analysis for expression patterns of the capsid (Cp) protein of West Nile virus (WNV) in three tumor cell lines.

In one aspect, the present invention provides a composition for treating or preventing a flavivirus or pestivirus infection comprising a Jab1 protein.

Viral infections and associated diseases intended to be treated or prevented according to the present invention are flavivirus and pestivirus infections. Flavivirus and pestivirus according to the classification of International Committee on Taxonomy of viruses, belong to the Flaviviridae family, which possesses a positive-stranded single strand RNA genome and has a natural host range including vertebrates and arthropods. Flavivirus and pestivirus virions consist of an envelope and a nucleocapsid. Flavivirus virions are spherical and 40-50 nm in diameter, and pestivirus virions are spherical to pleomorphic and 40-60 nm in diameter. Flavivirus and pestivirus have a very similar structure and infection mechanism and induce apoptosis of infected cells.

Flavivirus includes the mammalian tick-borne virus group, seabird tick-borne virus group, Aroa virus group, Dengue virus group, Japanese encephalitis virus group, Ntaya virus group, Kokobera virus group, Spondweni virus group, Yellow fever virus group, Entebbe virus group, Modac virus group and Rio Bravo virus group. The present composition may be preferably applied to an infection with the Japanese encephalitis virus group. The Japanese encephalitis virus group includes Cacipacore virus, koutango virus, Japanese encephalitis virus, Murray Valley encephalitis virus, St. Louis encephalitis virus, Usutu virus, West Nile virus, and Yaounde virus.

Pestivirus includes Border disease virus, bovine viral diarrhea virus 1, Bovine viral diarrhea virus 2, and Classical swine fever virus.

The present inventors, via a yeast two hybrid assay, found that Jab1 is a protein directly interacting with the capsid (Cp) protein of West Nile virus, which induces apoptosis in WNV-infected cells, and investigated the effect of Jab1 on the capsid protein. As a result, Jab1 was found to directly interact with the capsid protein, translocate the capsid protein from the nucleus to the cytoplasm and stimulate degradation of the capsid protein, thereby remarkably inhibiting apoptosis mediated by the viral capsid protein.

The Capsid denotes the protein shell that encloses the viral nucleic acid and is formed by multiple copies of a single major structural subunit protein. The structural subunit protein forming the capsid is called the capsid protein. With respect to the objects of the present invention, the capsid protein is the flavivirus or pestivirus capsid protein to which the Jab1 protein binds. The complete genome sequence of West Nile virus including the nucleic acid sequence of the capsid protein of West Nile virus, a member of flavivirus, is available from GenBank under accession numbers AF206518, AF196835, AF202541 and M12294. The nucleic acid sequences of capsid proteins of other members of flavivirus and pestivirus are also available from GenBank, for example, for JEV, under accession numbers M18370, D90194 and D90195; for SLEV, under accession number M16614; for YFV, under accession numbers AF094612, U17067, U17066, U54798, U21055, U21056 and X03700; for DENV, accession numbers M23027, U88535, U88536 and U88537); and for BVDV, accession number M31182.

The homology of the capsid protein between flavivirus and pestivirus, which possess the capsid protein capable of binding the Jab1 protein, is about 90%.

The Jab1 protein used in the present composition includes all Jab1 proteins derived from yeasts, plants and animals, which include a wild-type Jab1 protein and, as long as the function of binding to the flavivirus or pestivirus capsid protein and stimulating degradation of the capsid protein is retained, variants of the Jab1 protein made by deletions, insertions, non-conserveative or conservative substitutions, or combinations thereof. In one embodiment, the Jab1 protein may have an amino acid sequence designated as SEQ ID No. 2, and substitution, insertion and deletion variants of this amino acid sequence may be useful in the present composition.

The variant of Jab1 means the protein that has a sequence in which one or more amino acid residues differ from a wild-type amino acid sequence. An insertion is typically made by the addition of a consecutive amino acid sequence of about 1 to 20 amino acids, or may be made with a longer sequence. A deletion is typically in the range of about 1 to 30 amino acid residues, or may be in part made in a longer sequence such as the absence of one domain. Such variants may be prepared by a chemical peptide synthesis method or a DNA sequence-based recombinant method, which are known in the art (Sambrook et al., Molecular Cloning, Cold Spring Harbour Laboratory Press, New York, USA, 2d Ed., 1989). Amino acid exchanges in proteins and peptides which do not generally alter the activity of the protein or peptide are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

In addition, the Jab1 protein, if desired, may be modified by phosphorylation, sulfation, acrylation, glycosylation, methylation, farnesylation, and the like.

The variant or modified product may have the biological activity functionally identical to its natural form, or, if desired, may be made by altering the property of the natural form. It is preferably a protein that is improved in enhanced structural stability against heat, pH, etc., and protein activity by alteration and modification of its amino acid sequence.

The Jab1 protein may be obtained by extraction and purification from nature according to a method well known in the art (Merrifleld, J. Amer. chem. Soc. 85:2149-2156, 1963), or may be obtained using a genetic recombination technique.

When the protein is prepared by chemical synthesis, a polypeptide synthesis method well known in the art may be used.

In the case of using the genetic recombination technique, the Jab1 protein may be obtained by a process including inserting a nucleic acid coding for Jab1 into a suitable expression vector, transforming a host cell with the vector, cultivating the host cell to allow Jab1 to express and recovering expressed Jab1 from the cultured host cell.

As the expression vector for expressing the Jab1 protein, all common expression vectors may be used. Since expression levels and modification of proteins differ according to host cells, the most suitable host cell may be selected according to the intended use. Available host cells include, but are not limited to, prokaryotic cells such as *Escherichia coli, Bacillus subtilis, Streptomyces, Pseudomonas, Proteus mirabilis* or *Staphylococcus*. Among them, *E. coli* is most commonly used. In addition, useful as host cells are lower eukaryotic cells, such as fungi (e.g., *Aspergillus*) and yeasts (e.g., *Pichia pastoris, Saccharomyces cerevisiae, Schizosaccharomyces, Neurospora crassa*), insect cells, plant cells, and cells derived from higher eukaryotes including mammals.

After a protein is expressed in a selected host cell, it may be isolated and purified by a general biochemical isolation technique, for example, treatment with a protein precipitating agent (salting out), centrifugation, ultrasonic disruption, ultrafiltration, dialysis, and various chromatographies, such as molecular sieve chromatography (gel filtration), adsorption chromatography, ion exchange chromatography and affinity chromatography. Typically, these techniques are used in combinations of two or more to obtain highly pure isolation of a protein (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

In another aspect, the present invention provides a composition for treating or preventing a flavivirus or pestivirus infection comprising a nucleic acid having a nucleotide sequence coding for a Jab1 protein.

The Jab1-encoding nucleotide sequence in the present composition, which encodes the Jab1 protein in the form of a wild type or a variant as described above, may be altered by substitutions, deletions, insertions or combinations thereof of one or more bases, and may be naturally occurring or chemically synthesized.

The chemical synthesis of the Jab1-encoding nucleotide sequence may be carried out by a synthesis method well known in the art, for example, as described in the literature: Engels and Uhlmann, Angew Chem IntEd Engl., 37:73-127, 1988. Examples of the synthesis method include triester, phosphite, phosphoramidate and H-phosphate methods, PCR and other autoprimer methods, and oligonucleotide synthesis methods on solid phase supports.

In an embodiment, the Jab1-encoding nucleotide sequence is exemplified as a nucleotide sequence encoding the amino acid sequence of SEQ ID No. 2, preferably a nucleotide sequence designated as SEQ ID No. 1.

A nucleic acid having the aforementioned nucleotide sequence may be single-stranded or double-stranded, and may be DNA (genome, cDNA or synthetic) or RNA molecules.

In a preferred aspect, the Jab1-encoding nucleotide sequence is operably linked to a vector to provide a recombinant expression vector expressing the nucleotide sequence.

The term "vector", as used herein, means a vehicle for introducing a nucleic acid sequence (e.g., DNA, RNA, etc.) coding for a target gene into a host cell. Also, the term "expression vector", as used herein, which is a vector capable of expressing a target protein or target RNA in a suitable host cell, refers to a genetic construct that comprises essential regulatory elements to which a gene insert is operably linked thereto in such a manner as to be expressed in a host cell.

The term "operably linked", as used herein, refers to a functional linkage between a nucleic acid expression control sequence (such as a promoter) and a second nucleic acid sequence coding for a target protein or RNA in a manner that allows general functions. For example, when a nucleic acid sequence coding for a protein or RNA is operably linked to a promoter, the promoter may affect the expression of a coding sequence. The operable linkage to a recombinant vector may be prepared using a genetic recombinant technique well known in the art, and site-specific DNA cleavage and ligation may be carried out using enzymes generally known in the art.

The vector useful in the present invention includes plasmid vectors, cosmid vectors and viral vectors. A suitable expression vector includes expression regulatory elements, such as a promoter, an operator, an initiation codon, a stop codon, a polyadenylation signal and an enhancer, and a signal sequence or leader sequence for membrane targeting or secretion, and may be prepared in various constructs according to the intended use. The initiation and stop codons are generally considered to be a portion of a nucleotide sequence encoding an immunogenic target protein. Also, the initiation and stop codons are necessary to be functional in an individual to whom a genetic construct has been administered, and must be in frame with the coding sequence. The promoter of the vector may be constitutive or inducible. Also, the expression vector includes a selectable marker for selecting a host cell containing a vector, and, in the case of being replicable, includes a replication origin. The vector may be self-replicated or integrated into host DNA.

In a more preferred aspect, the present invention provides a composition comprising a recombinant viral vector carrying a nucleotide sequence coding for a Jab1 protein.

The term "recombinant viral vector", as used herein, typically denotes a viral vector that contains one or more exogenous genes, and, in the present invention, means a viral vector carrying a Jab1 gene. The viral vector is preferably a replication-defective vector that lacks a replicon.

Non-limiting examples of the recombinant vector include retrovirus, which is exemplified by HIV (Human Immunodeficiency Virus) MLV (Murine Leukemia Virus), ASLV (Avian Sarcoma/Leukosis Virus), SNV (Spleen Necrosis Virus), RSV (Rous Sarcoma Virus) and MMTV (Mouse mammary tumor virus), and recombinant viral vectors, which are exemplified by adenovirus, adeno-associated virus and herpes simplex virus.

The nucleic acid having a nucleotide sequence coding for a Jab1 protein may be delivered into target cells of a patient for treating or preventing a viral infection by a method known in the art, for example, direct injection of a vector in naked DNA form (Wolff et al., Science, 247:1465-8, 1990: Wolff et al., J Cell Sci. 103:1249-59, 1992), or using liposomes, cationic polymers, and the like. Liposomes are phospholipid membranes made by mixing cationic phospholipids such as DOTMA or DOTAP for gene delivery. When cationic liposomes are mixed with anionic nucleic acids in a predetermined ratio, nucleic acid-liposome complexes are formed. These complexes are internalized into cells by endocytosis and stay in the endosome (Schaefer-Ridder M et al., Science. 215(4529):166-168, 1982; Hodgson et al., Nat Biotechnol., 14(3):339-342, 1996). Release of an internalized gene from the endosome into the cytoplasm and transport of the endosomally released gene from the cytoplasm to the nucleus determine the efficiency for gene transfer and therapy. This gene transfer allows repeated administration and ensures high safety due to low immunogenicity, but has a disadvantage of providing low efficiency in gene expression. Cationic polymers used in gene transport include poly-L-lysine, spermine, polyethylenimine (PEI) and chitosan (Hashida, Br J Cancer., 90(6):1252-1258, 2004; Wiseman, Gene Ther., 10(19):1654-1662, 2003; Koping-Hoggard, Gene Ther., 8(14):1108-1121, 2001). When a gene is administered into the body in a complex form with a cationic polymer, in vivo detention time and expression duration of the gene remarkably increased in comparison with the case of being administered in naked DNA form.

In a further aspect, the present invention provides a composition for treating or preventing a flavivirus or pestivirus infection comprising a recombinant virus expressing a Jab1 protein.

Since the infection of cells of a patient with infective viral particles manipulated to express Jab1 in infected cells results in an increase in the expression efficiency of Jab1, this method provides a highly therapeutic effect.

Non-limiting examples of recombinant viruses useful in the present composition comprising a recombinant virus include retroviruses, adenoviruses, adeno-associated viruses and herpes simplex virus. Preferred are retroviruses and adenoviruses, and more preferred are adenoviruses.

Retroviruses have an advantage of providing long-lasting gene expression because they are irreversibly fused to the host chromosome. Adenoviruses, which are the most frequently used system in general gene therapy studies, are applicable to a wide spectrum of mammalian cells. Adeno-associated viruses have advantages of having a broad range of host cells where a therapeutic gene is delivered, fewer side effects on the immune system upon repeated administration and a long duration of gene expression. Herpes simplex virus is a highly neurotropic virus, which infects neural cells where its genome remains as a stable episomal element within the nucleus of neural cells without disturbing normal function of neural cells. When a replication-deficient herpes simplex virus was used for gene delivery, expression of a reporter gene in the nervous system was found to be sustained for a period of over one year.

In yet another aspect, the present invention provides a method of treating or preventing a flavivirus or pestivirus infection, which is base on administering, to a subject requiring treatment or prevention of a viral infection, a pharmaceutically effective amount of a Jab1 protein, a nucleic acid having a nucleotide sequence coding for a Jab1 protein or a recombinant virus expressing a Jab1 protein.

The Jab1 protein, nucleic acid having a nucleotide sequence coding for a Jab1 protein or recombinant virus expressing a Jab1 protein, used in the treatment method of the present invention, is the same as described above.

The treatment method of the present invention is provided for preventing or treating a viral infection in vertebrates, which includes mammals such as humans and livestock.

The pharmaceutical composition of the present invention, comprising the aforementioned Jab1 protein, nucleic acid having a nucleotide sequence coding for a Jab1 protein or recombinant virus expressing a Jab1 protein, is used for treating or preventing an infection of a virus belonging to the Flaviviridae family, preferably flavivirus or pestivirus. In particular, the present composition may be preferably used for treating or preventing a flavivirus infection. The aforementioned viruses are known to cause fever, rash, bleeding, jaundice, arthralgia, myalgia, encephalitis and meningitis (Watt et al., Am J Trop Med Hyg., 68(6):704-706, 2003; Anninger et al., Clin Infect Dis., 38(7):55-56, 2004). The pharmaceutical composition of the present invention may be used for suppressing or treating the incidence of the aforementioned diseases.

The present composition may include a pharmaceutically acceptable carrier. Examples of the pharmaceutically acceptable carrier may include, for oral administration, binders, lubricants, disintegrators, excipients, solubilizing agents, dispersing agents, stabilizing agents, suspending agents, pigments and aromatics; for injectable preparations, buffering agents, preservatives, analgesics, solubilizing agents, tonic adjusting agents and stabilizing agents; and for topical administration, bases, excipients, lubricants and preservatives. The pharmaceutical composition of the present invention may be formulated into a variety of dosage forms in combination with the aforementioned pharmaceutically acceptable carrier. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampoule as a single-dose dosage form.

The pharmaceutical composition of the present invention may be administered via any of the common routes, if it is able to reach a desired tissue. Therefore, the present composition may be administered topically, orally, parenterally, intranasally, intravenously, intramuscularly, subcutaneously, intraocularly and intradermally, and may be formulated into solutions, suspensions, tablets, pills, capsules and sustained release preparations. Injectable preparations are preferred. Injection may be carried out subcutaneously, intramuscularly and intravenously.

The present composition may be administered in a therapeutically or preventively effective amount. The dosage may vary according to the patient's age and sex, type and severity of the illness, administration routes, target cells and expression levels, and may be easily determined by an expert in the art.

In still another aspect, the present invention relates to a method of screening a compound stimulating expression of a Jab1 protein, comprising: (a) culturing a cell expressing the Jab1 protein; (b) contacting the cell cultured at (a) with candidate compounds for stimulating expression of the Jab1 protein; (c) comparing an expression level of the Jab1 protein at (b) with that in a control not contacted with the candidate compounds; and (d) identifying a compound increasing expression levels of the Jab1 protein.

In still another aspect, the present invention relates to a method of screening a compound stimulating interaction between a Jab1 protein and a capsid (Cp) protein, comprising: (a) culturing a cell transformed with both a recombinant vector expressing the Jab1 protein and another recombinant vector expressing the Cp protein of flavivirus or pestivirus; (b) contacting the cell cultured at (a) with candidate compounds for stimulating interaction between the Jab1 protein and the Cp protein; (c) comparing an expression level of the Cp protein at (b) with that in a control not contacted with the candidate compounds; and (d) identifying a compound reducing expression levels of the Cp protein.

In the above screening method, the Cp protein of flavivirus or pestivirus, and preferably the Cp protein of West Nile virus, may be used.

Decreased or increased expression levels of the Jab1 and Cp proteins may be detected in protein or mRNA levels.

Protein expression levels may be detected by electorphoresis where each protein is loaded onto a gel, and preferably by immunoassay where the amount of formed antigen-antibody complexes are assayed using an antibody to the Jab1 or Cp protein. Examples of these analysis methods include Western blotting, RIA and immunoprecipitation assay.

In the above detection method, the amount of antigen-antibody complexes formed may be quantitatively analyzed based on the size of signals of a detection label. The detection label may be selected from the group consisting of enzymes, fluorescent materials, ligands, luminescent materials, microparticles, redox molecules and radioisotopes, but the present invention is not limited to these examples.

The antigen-antibody complex formation may be detected using one selected from the group consisting of a colorimetric method, an electrochemical method, a fluorimetric method, luminometry, a particle counting method, visual assessment and a scintillation counting method, but the present invention is not limited to the examples.

mRNA expression levels may be detected by a method using primers specific for the Jab1 or Cp protein. Examples of the method include RT-PCR and Northern blotting. Preferred is RT-PCR, a simple analysis method that allows quantitative analysis of transcription of Jab1 or Cp to mRNA by analysis of band patterns and intensity.

The present invention will be explained in more detail with reference to the following examples in conjunction with the accompanying drawings. However, the following examples are provided only to illustrate the present invention, and the present invention is not limited to the examples.

EXAMPLE 1

Expression of the WNV-Cp Protein in Human Cells

To investigate the expression patterns of the WNV capsid (WNV-Cp) protein in various human cell lines, human kidney 293T cells (ATCC), osteosarcoma U2OS cells (ATCC), HeLa cells (ATCC) and human neuroblastma SK-N-SH cells (ATCC) were transfected with a vector carrying a WNV-Cp gene using a Lipofectamine reagent, and were subjected to immunofluorescent staining.

Figure 2:
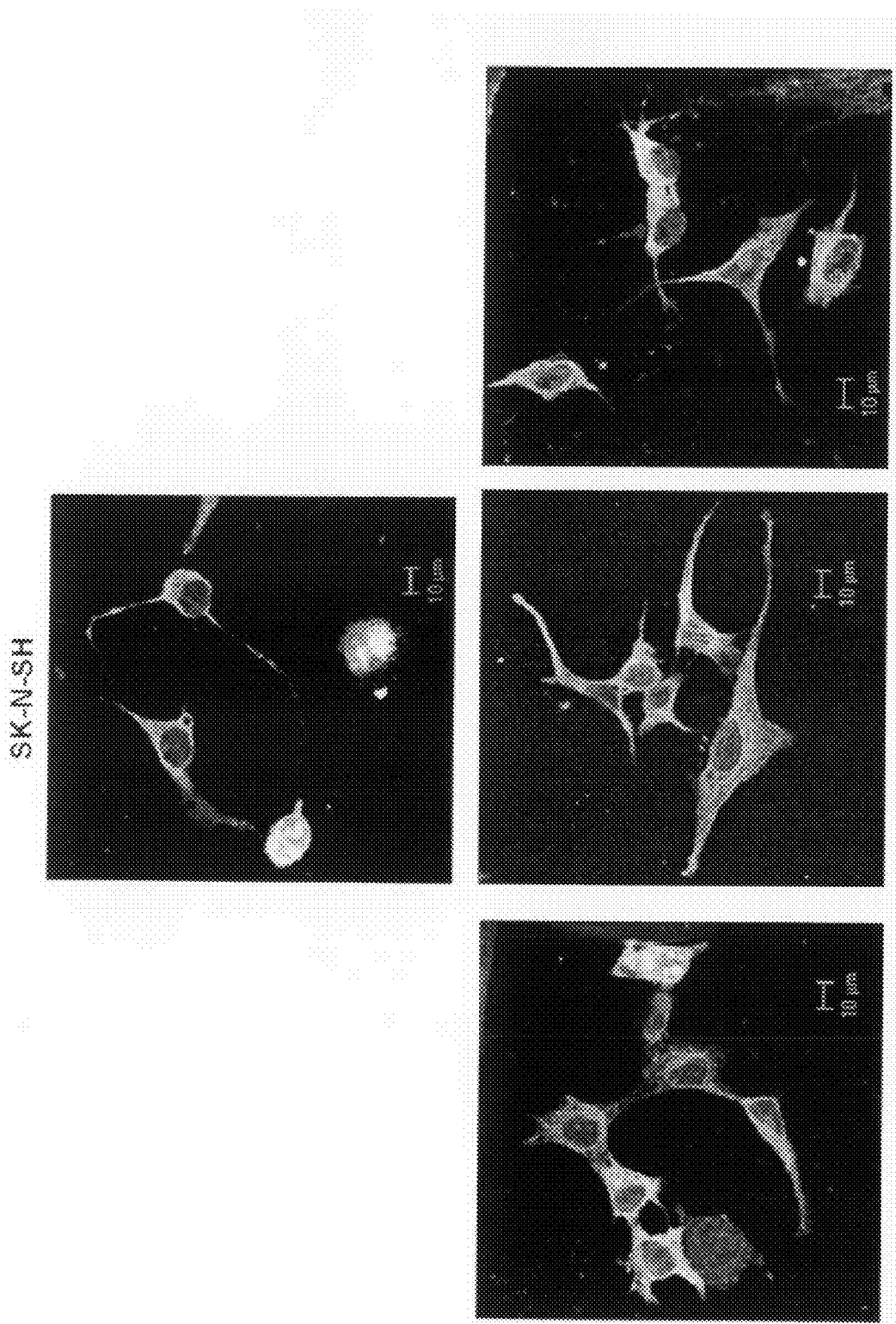
FIG. 2 shows the results of immunofluorescence analysis for expression patterns of WNV-Cp in SK-N-SH cells.

Primarily, a WNV-Cp gene was amplified by PCR using pcDNA3.1WNV-Cp as a template and primers designated as SEQ ID Nos. 3 and 4, and the WNV-Cp DNA was digested with EcoRI and XhoI and inserted into a pcDNA3HA plasmid, thus generating pcDNA3-HA/WNV-Cp. 293T, U2OS, HeLa and SK-N-SH cells were transfected with the pcDNA3-HA/WNV-Cp. After 24 hrs, the transfected cells were fixed and subjected to immunofluorescent staining using a primary HA-mouse monoclonal antibody (1:100 diluted; Santa Cruz) and a secondary fluorescein isothiocyanate (FITC)-conjugated antibody (1:100 diluted; Sigma). Then, the expression of WNV-Cp (green) was observed using a UV confocal microscope. Nucleus was stained with DAPI (blue). The WNV-Cp protein was found to exist in the nucleolus in 293T, U2OS and HeLa cells (FIG. 1) and in the cytoplasm in SK-N-SH cells (FIG. 2).

The existence in the cytoplasm of WNV-Cp present mainly in the nucleolus indicates that WNV-Cp interacts with some intracellular proteins.

EXAMPLE 2

Apoptosis Induction by WNV-Cp in Human Cells

The WNV-Cp protein is known to induce apoptosis by previous studies revealing that the WNV-Cp protein, in HeLa cells, induces nuclear condensation that is a typical feature of cells undergoing apoptosis, and such apoptosis occurs via the capase-9 pathway. In this test, these facts were confirmed by annexin-V staining and PI staining.

Figure 3:
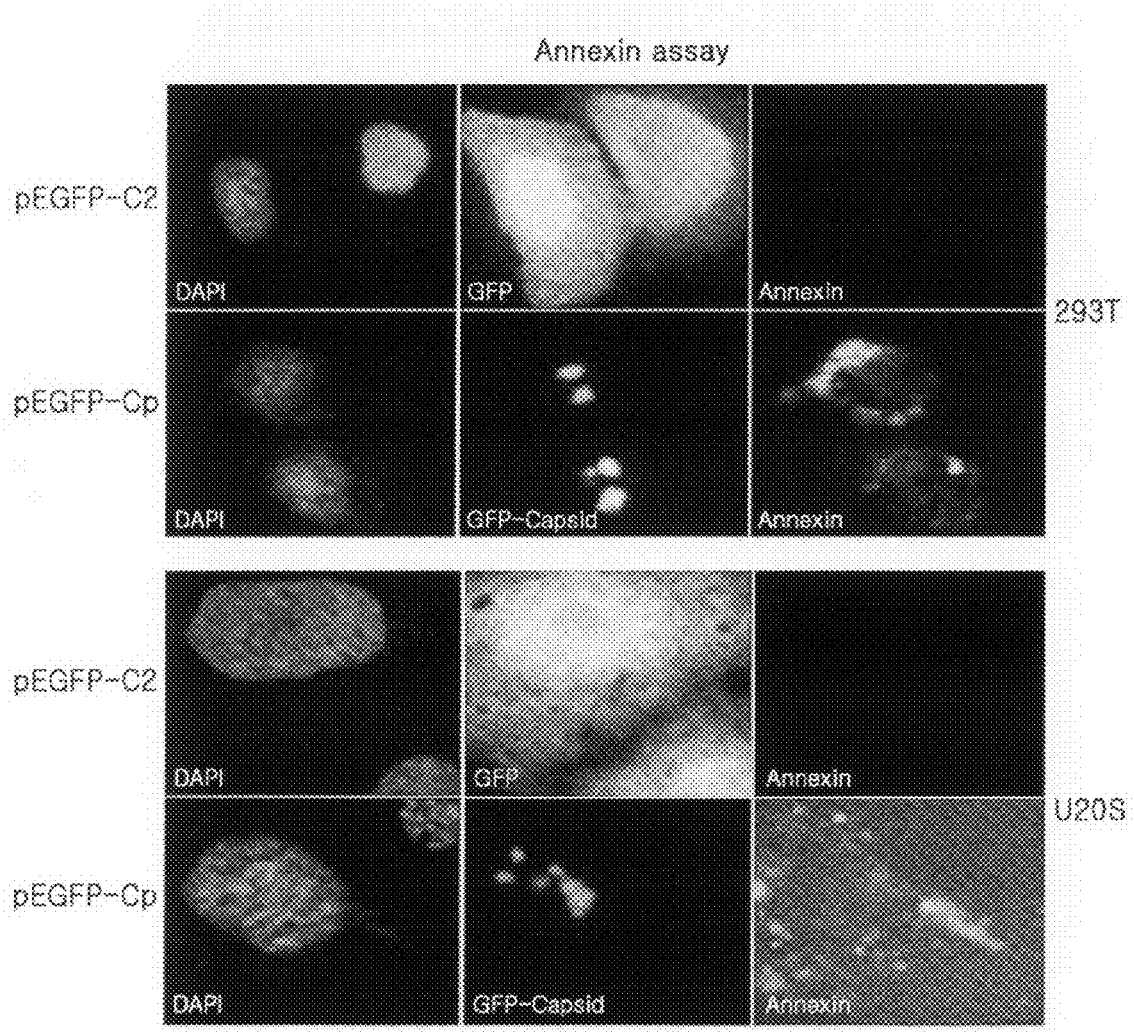
FIG. 3 shows the results of an annexin assay, displaying apoptosis induction by WNV-Cp in two tumor cell lines.

Primarily, a WNV-Cp gene was amplified by PCR using pcDNA3.1WNV-Cp as a template and primers designated as SEQ ID Nos. 3 and 7. The amplified WNV-Cp DNA was digested with EcoRI and BamHI and inserted into a pEGFP-C2 plasmid, thus generating pEGFP-WNV-Cp. Then, 293T and U2OS cells were individually transfected with a GFP expression vector, pEGFP-C2 (control vector; CLONTECH) and the pEGFP-WNV-Cp. After 24 hrs, the cells were stained with annexin-V (red) to bind annexin-V to an apoptosis indicator, phosphatidyl serine that is externalized upon apoptosis, and were observed under a Carl Zeiss vision microscope. As a result, apoptosis occurred in the cells with transfected the pEGFP-WNV-Cp (FIG. 3).

Figure 4:
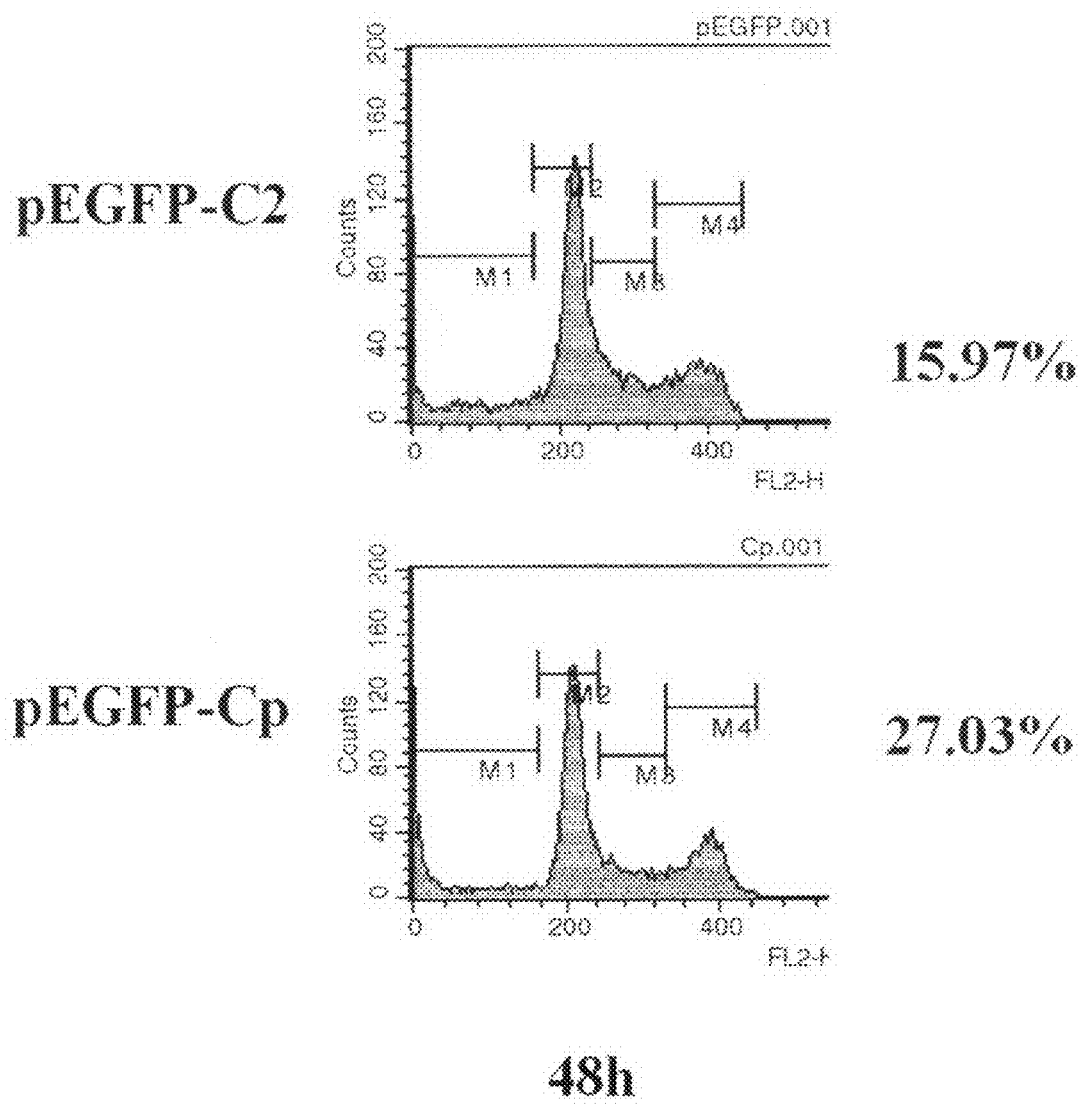
FIG. 4 shows the results of FACS analysis, displaying apoptosis induction by WNV-Cp in 293T cells.

Separately, 293T cells were transfected with pEGFP-C2 (control vector) and pEGFP-WNV-Cp. After 48 hrs, cell lysates were collected, stained with PI (propidium iodide) to measure apoptosis, and subjected to FACS analysis. The transfection with the control vector pEGFP resulted in an apoptosis rate of 15.97%, and the transfection with the pEGFP-WNV-Cp resulted in an apoptosis rate of 27.03% (FIG. 4).

EXAMPLE 3

Screening for Proteins Interacting with WNV-Cp

A possible mechanism of the apoptosis induction by WNV-Cp involves direct or indirect interaction of the capsid protein with regulators capable of causing apoptosis. In this regard, to better understand the apoptosis induction by the capsid protein, the regulators interacting with WNV-Cp need to be screened. For screening the regulators, a yeast two hybrid assay was performed using a cDNA library from human brain tissue that is a major infection site of West Nile virus.

Primarily, a WNV-Cp gene (450 bp) was amplified by PCR using pcDNA3.1 WNV-Cp as a template and primers designated as SEQ ID Nos. 3 and 4, below. The amplified WNV-Cp gene was cloned into EcoRI/SalI sites of a pGBK-T7 vector containing a TRP1 marker and a Ga14-DNA binding domain, thus generating a pGBK-T7 WNV-Cp construct.

Forward primer (SEQ ID No. 3):
5'-CCG GAA TTC TCT AAA AAA CCA GGT GGC CCC GG-3'

Reverse primer (SEQ ID No. 4):
3'-CCG CTC GAG CTA CGC GCC CAC GCT GGC GAT CAG-5'

Figure 5:
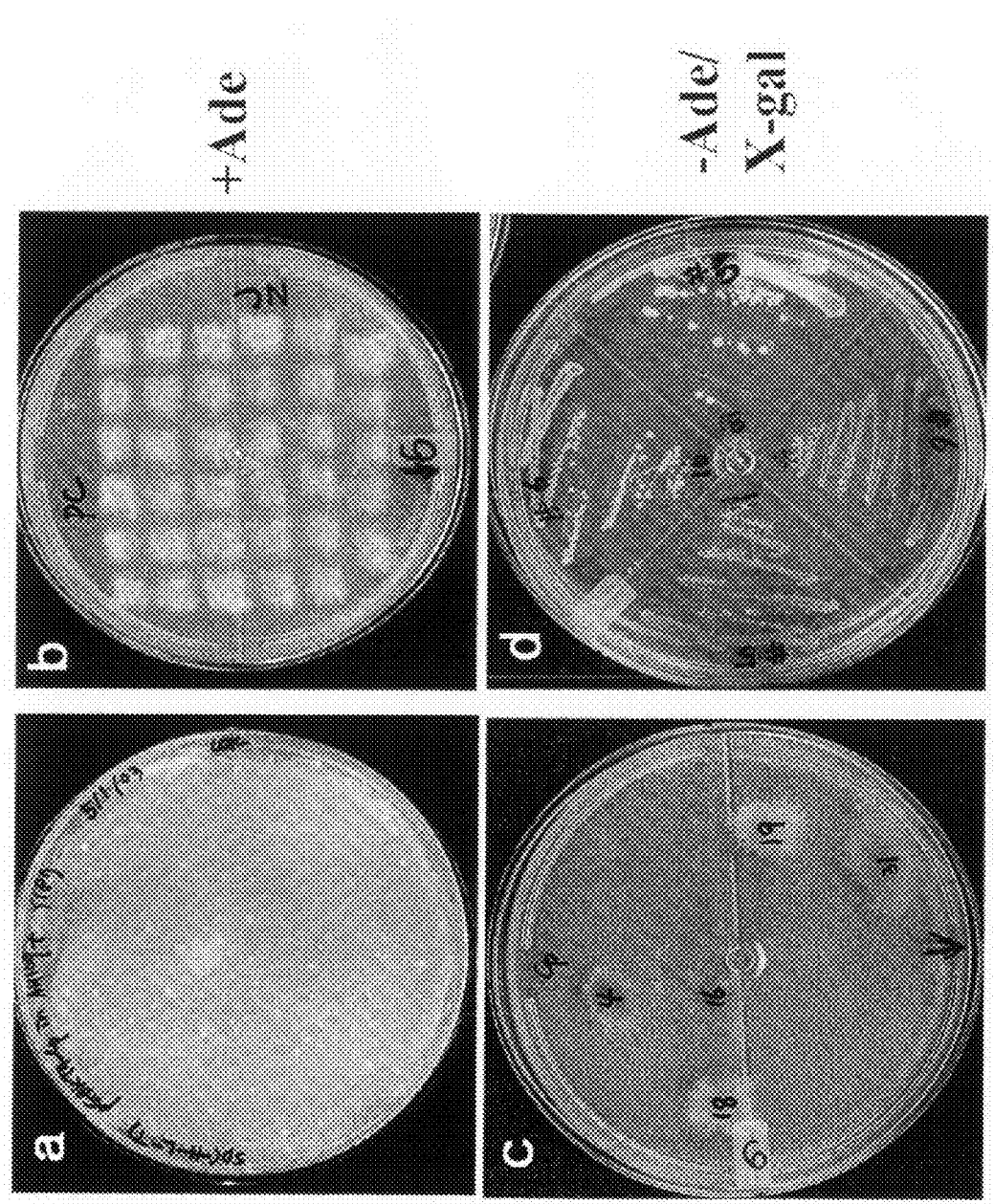
FIG. 5 shows the procedure of a yeast two hybrid assay resulting in obtainment of clones expressing proteins interacting with WNV-Cp.

The yeast two hybrid assay was carried out using the pGBK-T7 WNV-Cp plasmid as a bait and, as a prey, a human brain cDNA library (Clontech) carrying the LEU2 marker and fused to the downstream of the Gal4 activation domain. A yeast strain AH109 was transfected with the bait plasmid pGBK-T7 WNV-Cp by a lithium acetate method (Gietz et al. 1995), mixed for mating with another yeast strain Y187 transfected with 1 ml of the human brain cDNA library, and smeared onto fifty 150-mm SD plates lacking adenine, leucine, histidine and tryptophan. 945 colonies were obtained (the a of FIG. 5), and candidates to have the potential to interact with the capsid protein were selected on the same plate (the b of FIG. 5). For second screening, replica plating was carried out on the selection medium, SD/-Ade-Leu-His-Trp, and blue colonies were obtained (the c of FIG. 5). The blue colonies were tested again, and eventually, eighty clones were obtained (the d of FIG. 5). Yeast plasmid was isolated from the clones by lyticase-based cell disruption and subjected to DNA sequencing using primers designated as SEQ ID Nos. 5 and 6, below, followed by blast searching for identifying corresponding proteins.

Forward primer
(SEQ ID No. 5)
5'-CTA TTC GAT GAT GAA GAT ACC CCA CCA AAC CC-3'

Reverse primer
(SEQ ID No. 6)
3'-AGT GAA CTT GCG GGG TTT TTC AGT ATC TAC GAT-5'

Eight proteins were identified, which were Jab1, TPR1, RanBPM (RanBP9), PAP-1BP, Snapin (Synaptosomal-associated protein), Bassoon protein, a likely ortholog of mouse rabphilin3A and CG13214-PA.

EXAMPLE 4

Translocation of WNV-Cp by Jab1

Figure 6:
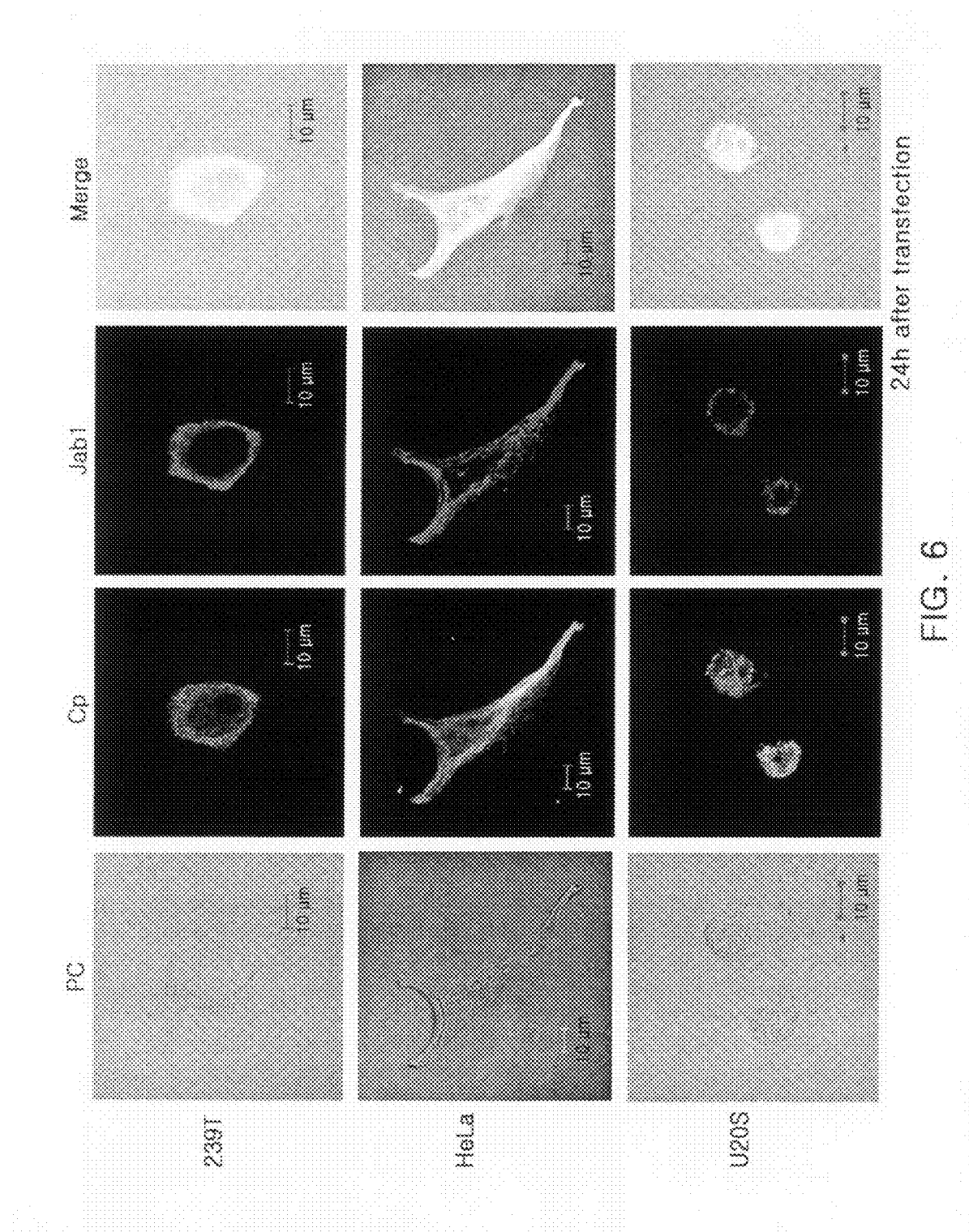
FIG. 6 shows the results of immunofluorescence analysis, revealing that Jab1 translocates WNV-Cp from the nucleolus to the cytoplasm.

To evaluate the effect of Jab1, identified to interact with WNV-Cp, on the intracellular location of WNV-cp, 293T, U2OS and HeLa cells were cotransfected with the WNV-Cp protein and Jab1. 293T, U2OS and HeLa cells were cotransfected with HA-tagged pcDNA-HA/WNV-Cp and Flag-tagged pCMV Tag2B-Jab1. After 24 hrs, the cells were stained using an anti-HA antibody (green) and an anti-Flag antibody (red) and observed under a confocal microscope. As shown in FIG. 6, like Jab1, the immunofluorescence signal for WNV-Cp appeared in the cytoplasm. A merge of two confocal images shows that WNV-Cp and Jab1 are expressed in the same site, cytoplasm, and PC (phase contrast) displays the whole cell morphology.

Figure 7:
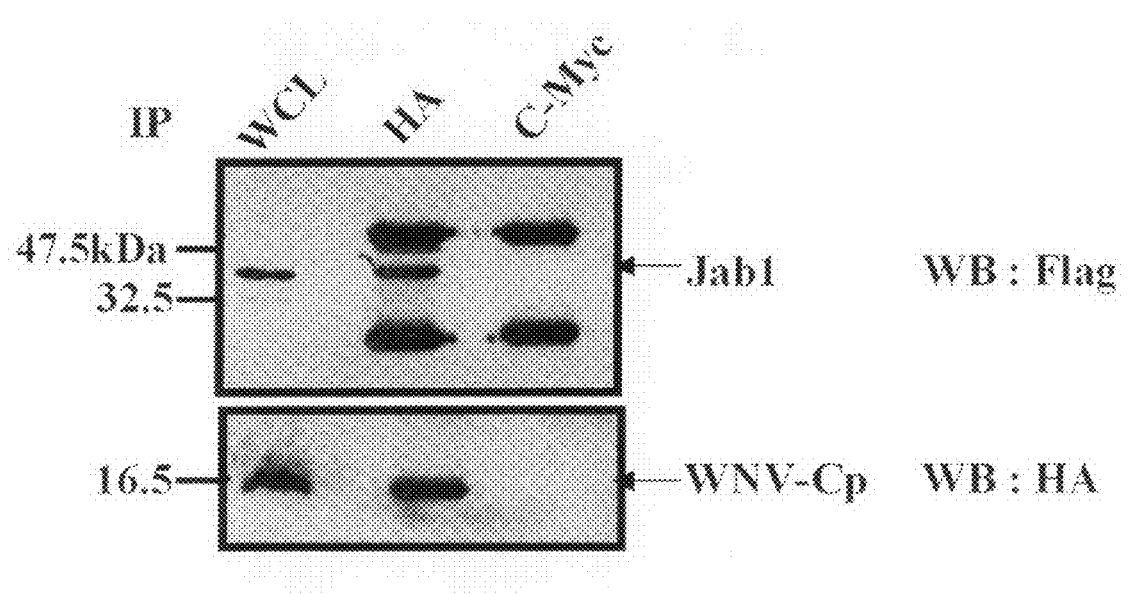
FIG. 7 shows the results of immunoprecipitation, revealing that Jab1 interacts with WNV-Cp.

Separately, immunoprecipitation (IP) was performed to confirm the interaction between WNV-Cp and Jab1. 293T cells were cotransfected with Flag-Jab1 and HA-WNV-Cp plasmids, and the whole cell lysates were immunoprecipitated with an anti-HA mouse antibody. As a control, IP was carried out with an anti-Myc antibody. Immunoprecipitated proteins were run on a 12% SDS-PAGE gel, transferred to a nitrocellulose membrane, and detected with an anti-Flag mouse antibody to visualize immunoprecipitated Jab1 along with WNV-Cp (FIG. 7).

Jab1 was found to be co-immunoprecipitated with WNV-Cp. This result indicates that Jab1 interacts with WNV-Cp in 293T cells and translocates WNV-Cp from the nucleolus to the cytoplasm.

EXAMPLE 5

Inhibition of WNV-Induced Apoptosis by Jab1

WVP-Cp, which is a pathogenic protein, is known to induce apoptosis via the mitochondrial/caspase-9 pathway. In this regard, a caspase activity assay was performed to evaluate the effect of Jab1 on WVP-Cp-induced apoptosis.

Figure 8:
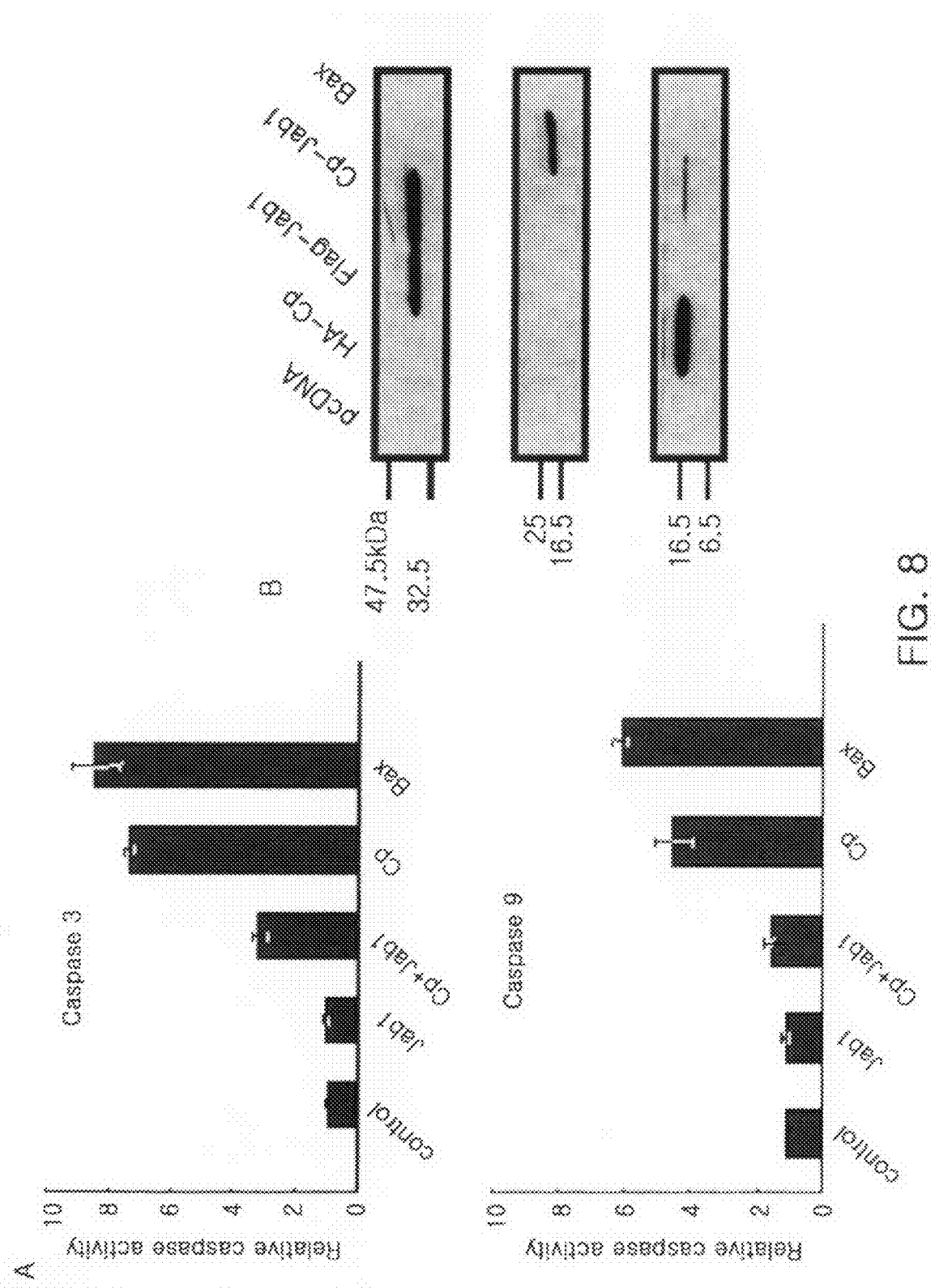

293T cells were plated onto 60-mm plates at a density of $3 \times 10^5$ cells, cultured, and transfected with pcDNA3-HA, pcDNA3-HA/Cp, pCMV-tag2B-Jab1, both pcDNA3-HA/Cp and pCMV-tag2B-Jab1, and pcDNA3-Bax, respectively. After 24 hrs, the cells were washed with 1×PBS twice, transferred to 1.5-ml tubes, and lysed with 20 µl of buffer C (25% glycerol, 0.42 M NaCl, 1.5 M $MgCl_2$, 0.2 mM EDTA, 20 mM HEPES, 1 mM DTT, 0.5 mM PMSF, pH7.9). After being incubated for 10 min on ice, the lysed cells were centrifuged. The total protein concentration in each supernatant was measured, and samples of zero to 300 µg of proteins were placed into a 96-well plate. To the 96-well plate, 50 µl of 2× reaction buffer and 5 µl of 4 mM DNA-conjugated substrate, provided in a caspase colorimetric substrate set II plus kit (Biovision), were added. After a 1-hr incubation at 37° C., the activity of caspase-3 and caspase-9 was measured at 410 nm using a microtiter plate reader. The results are given in the A panel of FIG. 8. In cells expressing WNV-Cp, the activity of capase-3 and caspase-9 was similar to that in cells expressing Bax, a member of the pro-apoptotic Bcl-2 family. When cells co-expressed WNV-Cp and Jab1, the caspase activity was remarkably reduced. These results indicate that Jab1 suppresses the activation of caspase-3 and caspase-9 by WNV-Cp. The expression of the proteins used in this caspase activity assay was detected by Western blotting, and the results are given in the B panel of FIG. 8.

Taken together, these results indicate that Jab1 expressed in the cell suppresses WNV-Cp-induced apoptosis through the mitochondrial/caspase-9 pathway by translocating WNV-Cp from the nucleolus to the cytoplasm.

EXAMPLE 6

Degradation of WNV-Cp by Jab1

To determine whether Jab1 stimulates degradation of WNV-Cp, protein levels of WNV-Cp were assessed in cells treated with a 26S proteasome inhibitor, LLnL (Sigma).

293T cells were plated onto 60-mm plates at a density of $3\times10^5$ cells, cultured, and transfected with pcDAN3-HA/WNV-Cp alone, and pcDAN3-HA/WNV-Cp and pCMV-tag2B-Jab1 together using an Effectene transfection reagent (Qiagen). In the case of the co-transfection, to equalize the levels of expressed DNA, 12 hrs after transfection, cells were divided into two plates by pipetting. 20 hrs after transfection, the cells were treated for 4 hrs with 20 μM/ml of the proteasome inhibitor LLnL (N-acetyl-L-luecinyl-norleucinal, Sigma). Then, the cells were washed with 1×PBS and collected. Samples of 50 μg protein were loaded onto a SDS-PAGE gel and analyzed by Western blotting using an anti-HA antibody (Santa Cruz) for the detection of WNV-Cp expression and an anti-Flag M2 antibody (Sigma) for the detection of Jab1 expression. Actin was used as a loading control.

Figure 9:
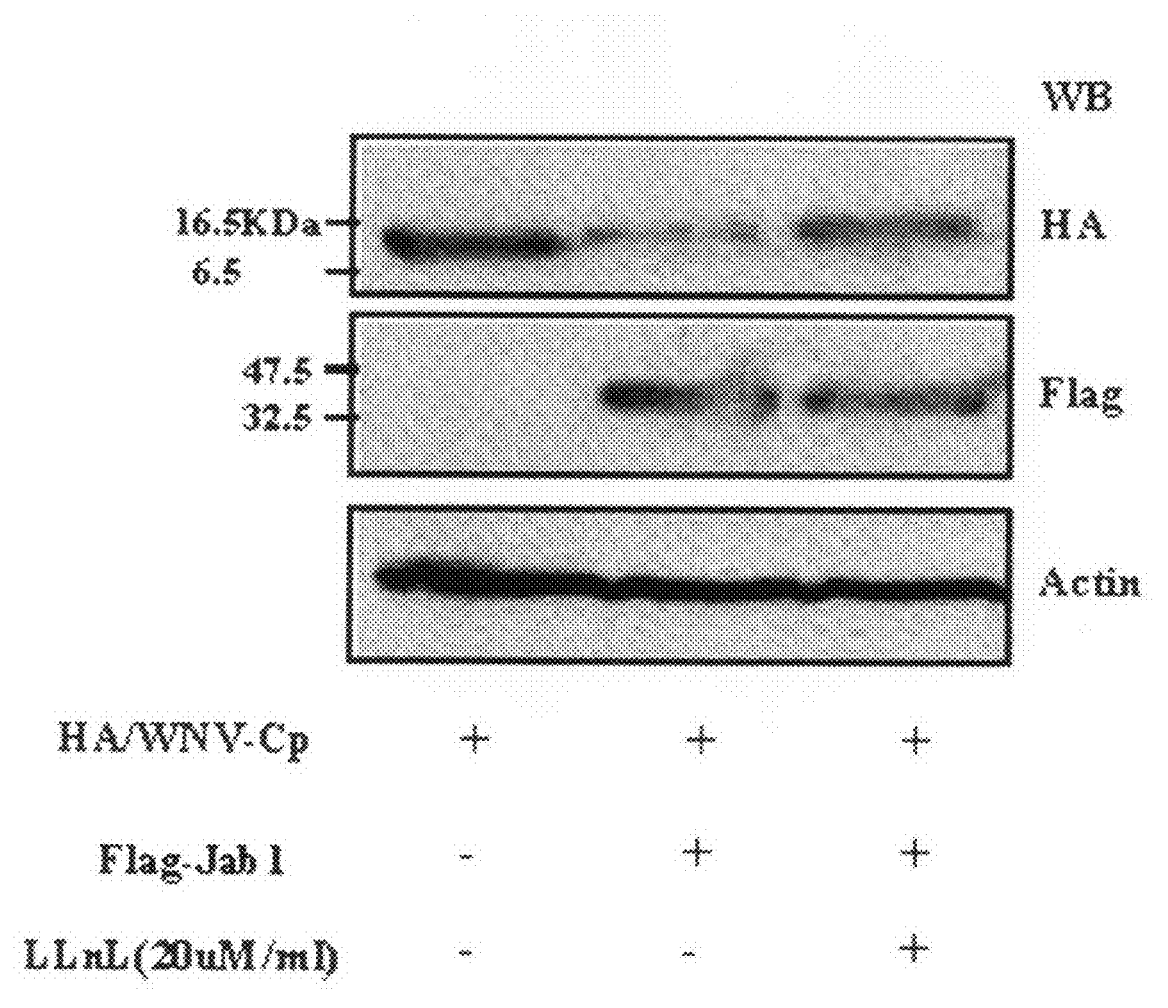

Compared to the single expression of WNV-Cp, the coexpression with Jab1 resulted in a large decrease in protein levels of WNV-Cp (lanes 1 and 2 of FIG. 9). In contrast, upon the treatment with LLnL, the cotransfected cells exhibited increased protein levels of WNV-Cp (lane 3 of FIG. 9). These results indicate that Jab1 accelerates the degradation of WNV-Cp.

Taken together, these results indicate that Jab1 suppresses the function of WNV-Cp by inducing the degradation of WNV-Cp through the ubiquitin proteasome pathway.

EXAMPLE 7

Inhibition of Apoptosis Using Signal Transduction Pathway Regulators

Human neuroblastoma SH-SY5Y cells were transfected with a WNV-Cp gene. To determine an apoptosis rate in cells expressing the capsid protein of WNV, the cells were stained with annexin V-PE and subjected to FACS analysis (BioRAD, Win BRYTE). As a result, the cells were fractionated into four fractions: A, B, C and D. The A fraction indicates a cell population that was not injected with the WNV-Cp gene and stained with annexin V-PE. The B fraction displays a cell population that was injected with the WNV-Cp gene and stained with annexin V-PE. The C fraction displays a cell population that was not injected with the WNV-Cp gene and not stained with annexin V-PE. The D fraction displays a cell population that was injected with the WNV-Cp gene and not stained with annexin V-PE.

Figure 10:
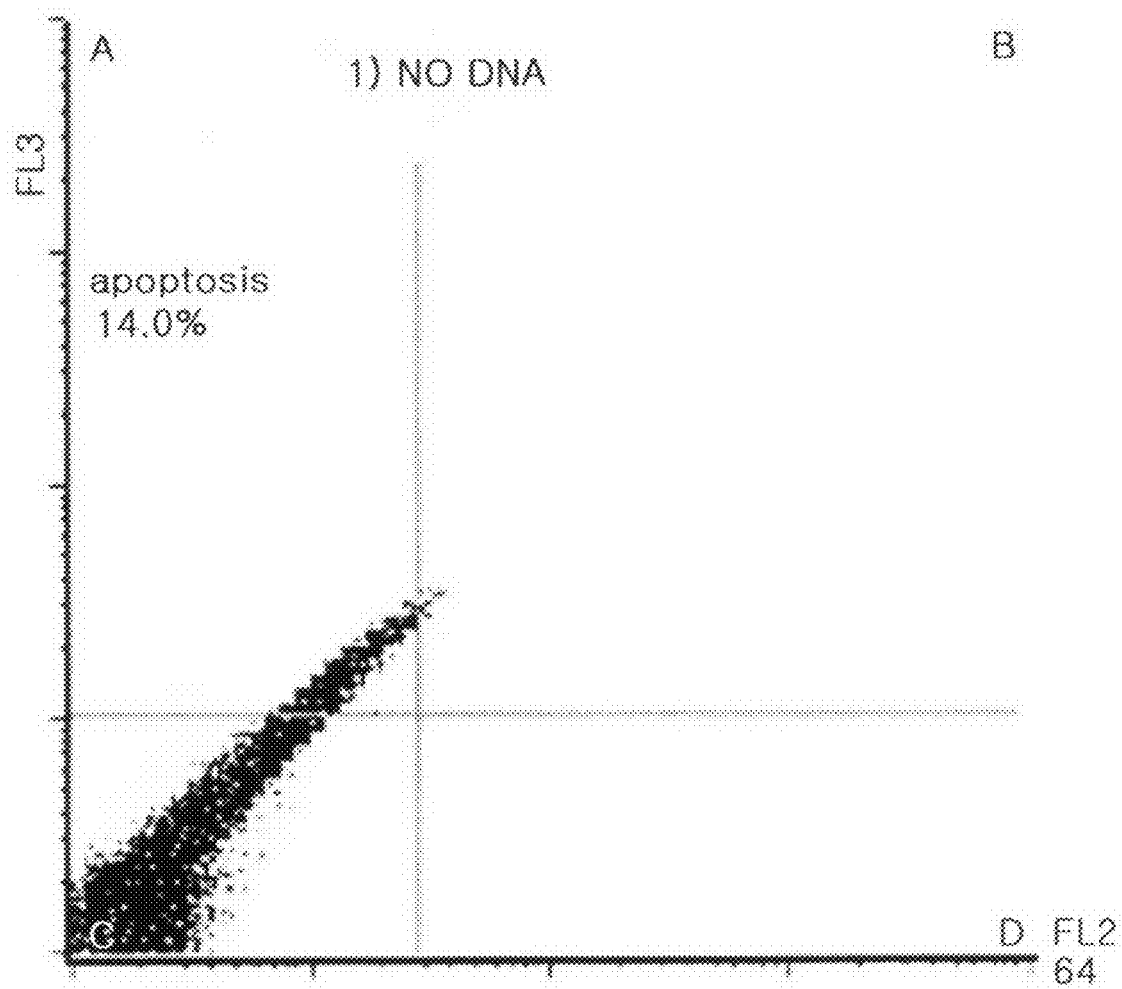
FIG. 10 shows the results of FACS analysis, displaying an apoptosis rate of normal cells not transfected with a C2-Cp gene.
Figure 11:
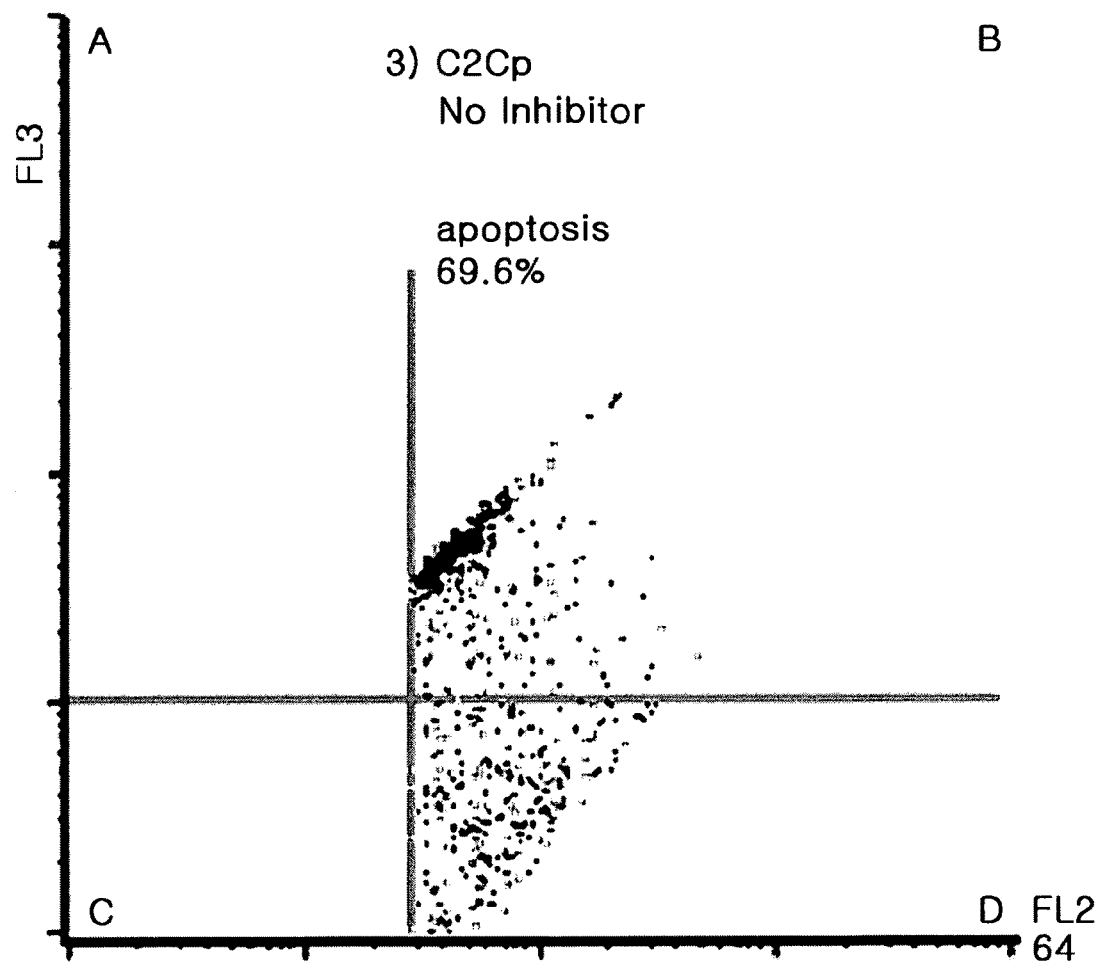
FIG. 11 shows the results of FACS analysis, displaying an apoptosis rate of cells transfected with a pEGFP-C2-Cp plasmid.
Figure 12:
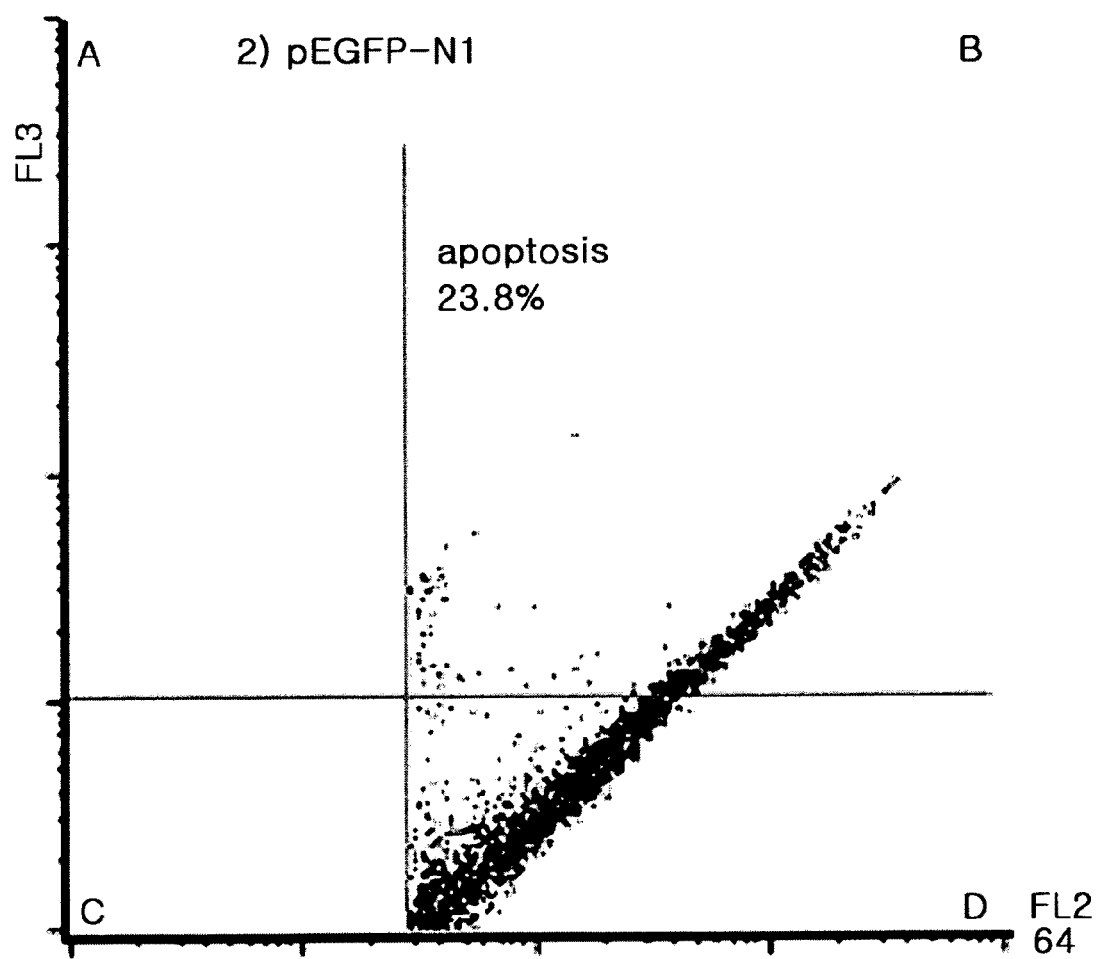
FIG. 12 shows the results of FACS analysis, displaying an apoptosis rate of cells transfected with a pEGFP-N1 plasmid.

Normal cells not injected with a C2-Cp gene displayed an apoptosis rate of 14.0% (FIG. 10), and cells expressing WNV-Cp exhibited an apoptosis rate of 69.6% (FIG. 11). These results confirmed that WNV-Cp greatly increases apoptosis of cells. As a negative control, pEGFP-N-1-injected cells showed an apoptosis rate of 23.8% (FIG. 12), which was higher than as expected. This high apoptosis rate in the negative control is believed to be due to an EGFP signal being very strong and thus cross-linked with a FL2 signal, and may therefore be substantially lower.

Separately, SH-SY5Y cells were transfected with a WNV-Cp gene. After 6 hrs, the cells were treated with 200 nM of a PI3K inhibitor, wortmanin (Sigma), and 5 μM and 50 μM of an Akt inhibitor, calbiochem (CN Biosciences). After 24 hrs, the cells were stained with annexin V-PE that is capable of detecting a step of apoptosis and subjected to FACS analysis (BioRAD, WinBryte) for measuring an apoptosis rate. About 10-30% of the cells were found to be successfully transfected with the WNV-Cp gene. The transfected cells were analyzed on a FL3 channel (green fluorescence) and annexin V-PE binding was analyzed on a FL2 channel. An apoptosis rate in capsid-expressing cells was calculated according to Reaction 1, below. Cells transfected with a pEGFP-N1 plasmid were used as a negative control, and cells transfected with a C2-Cp plasmid and not treated with the inhibitor were used as a positive control.

[Annexin V-PE-positive cells/(all cells expressing C2−Cp)]×100    [Reaction 1]

Figure 13:
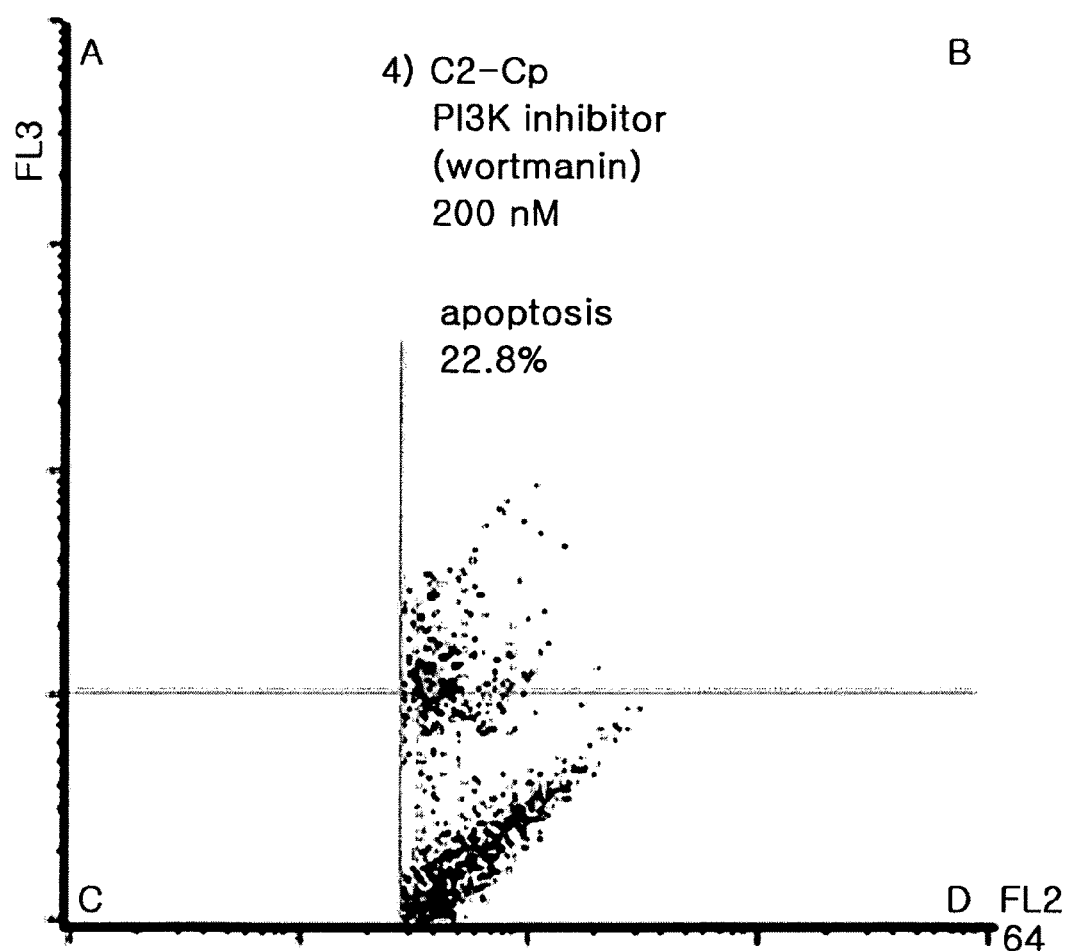
FIG. 13 shows the results of FACS analysis, displaying an apoptosis rate of cells transfected with a pEGFP-C2-Cp plasmid and treated with 200 nM of a PI3K inhibitor.
Figure 14:
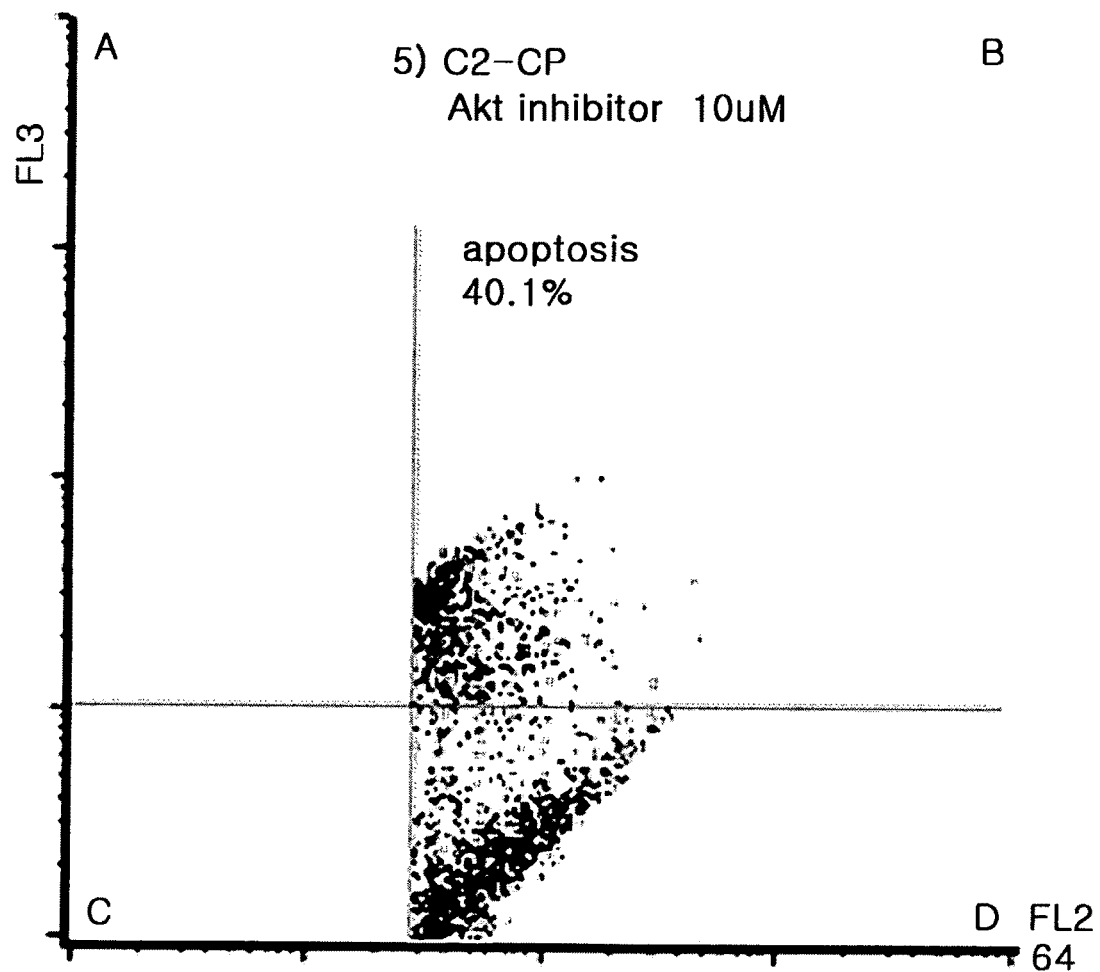
FIG. 14 shows the results of FACS analysis, displaying an apoptosis rate of cells transfected with a pEGFP-C2-Cp plasmid and treated with 5 µM of an Akt inhibitor.
Figure 15:
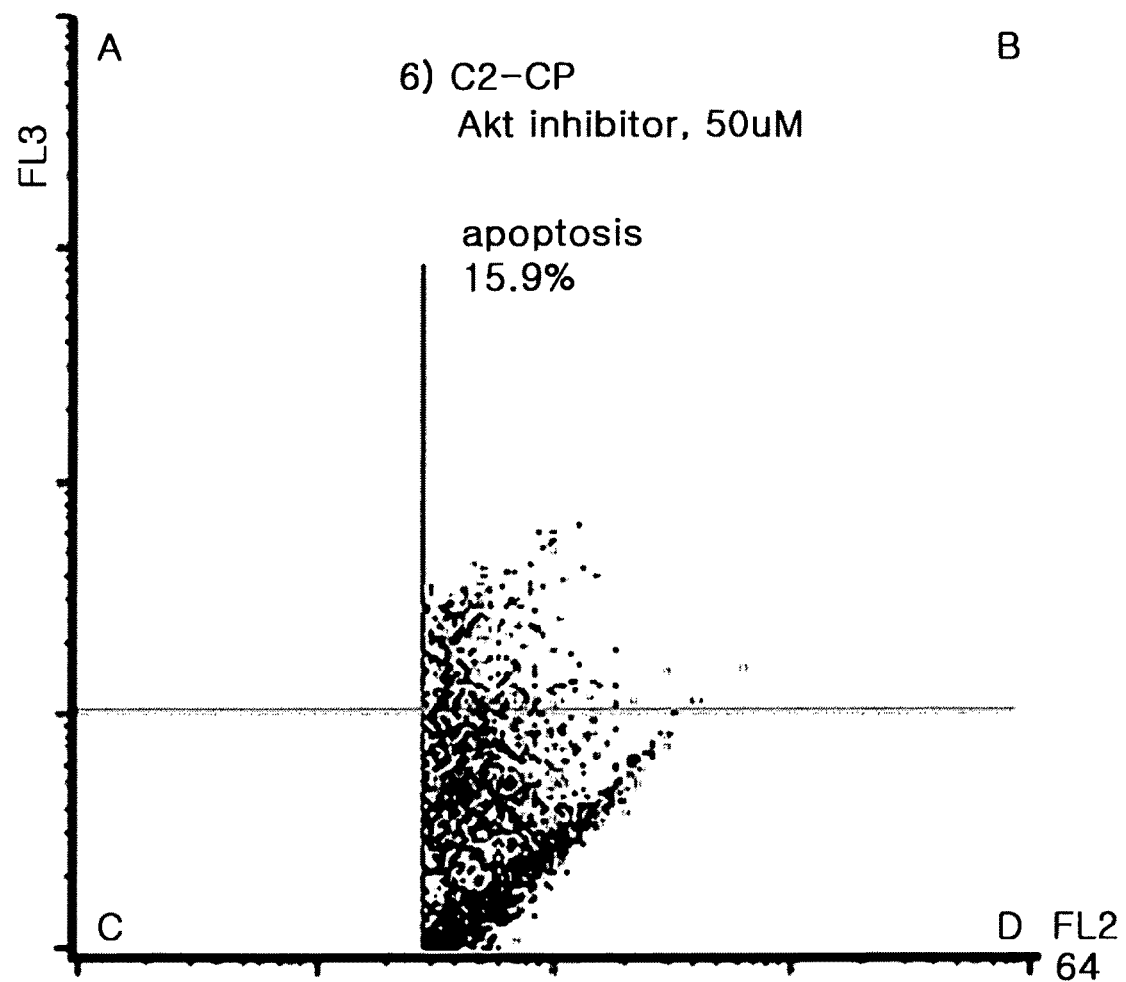
FIG. 15 shows the results of FACS analysis, displaying an apoptosis rate of cells transfected with a pEGFP-C2-Cp plasmid and treated with 50 µM of an Akt inhibitor.

Cells expressing WNV-Cp displayed an apoptosis rate of 69.6%. In contrast, when treated with 50 μM of the Akt inhibitor calbiochem and 200 nM of the PI3K inhibitor wortmanin, these cells exhibited apoptosis rates of 15.9% and 22.8%, respectively. That is, the treatment of the inhibitors resulted in suppression of apoptosis induced by WMV-Cp (FIGS. 13,14 and 15). These results indicate that the PI3K inhibitor and Akt inhibitor suppress the apoptosis induced by the expression of WNV-Cp.

EXAMPLE 8

Decreased Expression of Endogenous p53 by Jab1

The COP9 signalosome-specific phosphorylation targets the tumor suppressor gene p53 to degradation by the ubiquitin-26S proteasome-dependent pathway (Bech-Otschir et al., EMBO J., 20(7):1630-1639, 2001). On the assumption that Jab1 interacts with p53 because it is a member of the COP9 signalosome, Jab1 was evaluated for its effect on p53 expression.

Figure 16:
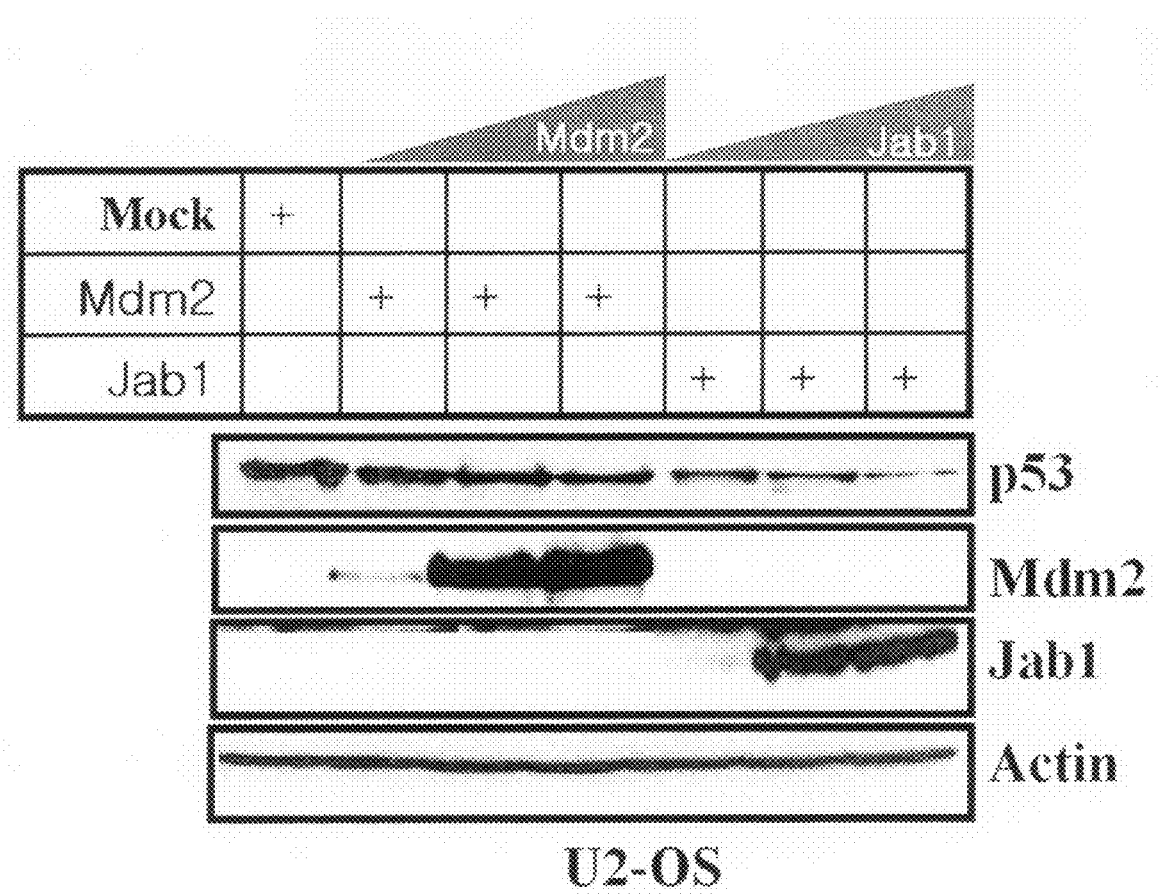
FIG. 16 shows the results of Western blotting, displaying that p53 expression decreases with increasing concentrations of Jab1.

U2OS cells were transfected with Flag/mdm2 (control) and Flag/Jab1 with various concentrations of 1, 3 and 5 μg using a Lipofectamin/plus reagent (Invitrogen). After 48 hrs, cell lysates were collected, and total protein concentrations were measured by a BSA (PIERCE) method. Samples of 100 μg/ml protein were separated on a 10% SDS-PAGE gel and transferred to a nitrocellulose membrane. The blot was blocked with 5% skim milk for 30 min, and treated with a rabbit anti-HA antibody (Santa Cruz) and a mouse anti-Flag antibody (Sigma) to examine expression levels of p53 according to increased expression of mdm2 and Jab1. Expression of p53 was rarely affected by the control mdm2, but remarkably decreased with increasing concentrations of Jab1 (FIG. 16).

EXAMPLE 9

Establishment of Jab1 Adenovirus Stable Cell Line

Figure 17:
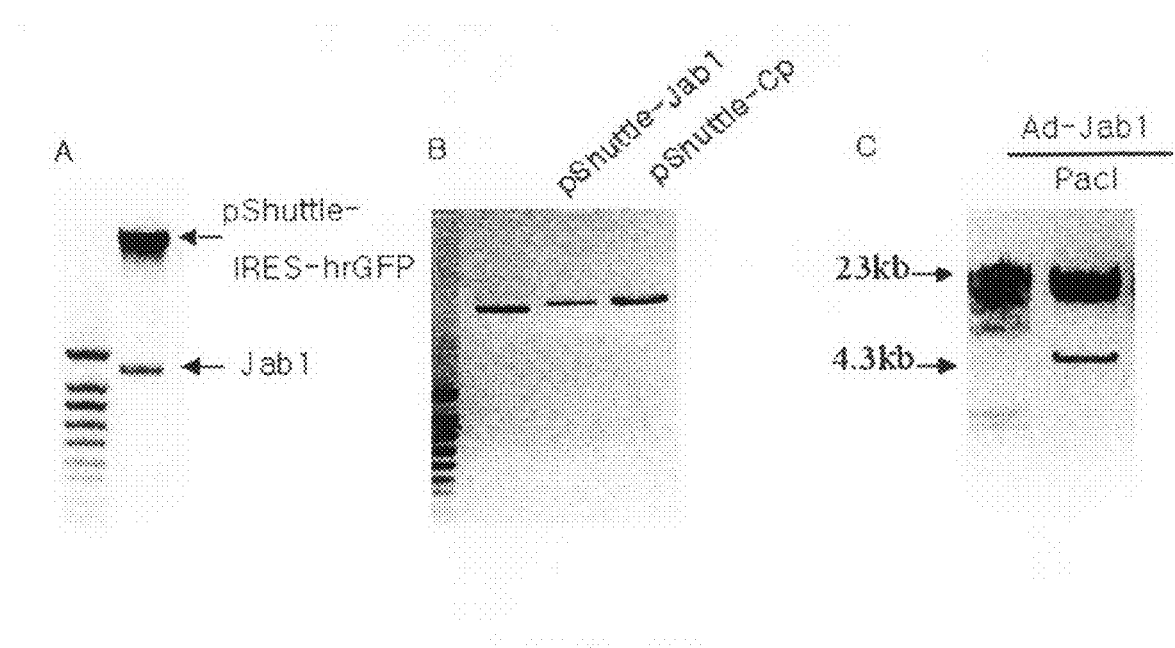
FIG. 17 shows the determining of an expression of a vector for establishing a Jab1 adenovirus stable cell line, wherein FIG. 17A refers to the results for western blotting for pShuttle-IRES-hrGFP and Jab1.

A stable cell line producing an adenovirus inducing overexpression of Jab1 was established using an AdEasy XL adenoviral vector system (Stratagene). Jab1 was cloned into BglII/PvuI sites of a pShuttle-IRES-hrGFP vector (the A and B of FIG. 17). The resulting pShuttle-IRES-hrGFP/Jab1 vector was purified by maxi preparation (maxi-prep), digested with PmeI, and transformed into an E. coli strain BJ5183 which contains AD1 (Stratagene) to produce homologous recombinant adenovirus plasmid. Emerged colonies were picked and grown in a culture broth, and plasmid DNA was isolated from the culture. Cloning was found to be successful by restriction mapping with PacI (the C of FIG. 17). The plasmid was then amplified by being transfected into mammalian AD293 cells (Stratagene) using a Lipofectamin/plus reagent (Invitrogen). Produced adenovirus was transfected again into AD293 cells, thus generating a stable cell line producing a recombinant adenovirus carrying a Jab1 gene, that is, a Jab1 adenovirus stable cell line.

The Ad1-Jab1 plasmid used in the production of the adenovirus stable cell line was deposited at an international depositary authority, KCCM (Korean Culture Center of Microorganisms; 2nd Floor, Yourim Building, 361-221, Hongje 1-dong Seodaemun-gu, Seoul, Korea) on Aug. 31, 2004, and assigned accession number KCCM 10593.

EXAMPLE 10

Establishment of NIH3T3 Jab1 Stable Retrovirus Cell Line

A HA/Jab1 fragment excised from the pcDNA3-HA/Jab1 plasmid was subcloned into an EcoRI site of the pLPCX retroviral vector (BD Bioscience) capable of producing retrovirus, thus generating pLPC/HA-Jab1. The pLPC/HA-Jab1 construct carrying a puromycin resistant gene was cotransfected with the pCL packaging plasmid (BD Bioscience) into 293T cells using a Lipofectamine reagent (Invitrogen). After two days, viral particles were purified with a 0.45-μm filter. 1 ml of the viral particles was diluted in 2 ml of medium and supplemented with 4 μg/ml polybren (Sigma) helping viral infection, and infected NIH3T3 cells. After 24 hrs, the cells were selected in a medium containing 2 μg/ml puromycin (Sigma), thereby generating a stable cell line producing a recombinant retrovirus carrying a Jab1 gene, that is, a Jab1 retrovirus stable cell line. A recombinant retrovirus produced by the stable cell line, Retro-Jab1, was deposited at an international depositary authority, KCCM (Korean Culture Center of Microorganisms; 2nd Floor, Yourim Building, 361-221, Hongje 1-dong Seodaemun-gu, Seoul, Korea) on Aug. 31, 2004, and assigned assess number KCCM 10592. In a control cell line not carrying an exogenous Jab1 gene and the retrovirus stable cell line highly expressing Jab1, expression levels of Jab1 and p53 were examined. The retrovirus stable cell line displayed high expression of Jab1 and decreased expression of p53 (FIG. 18).

Figure 18:
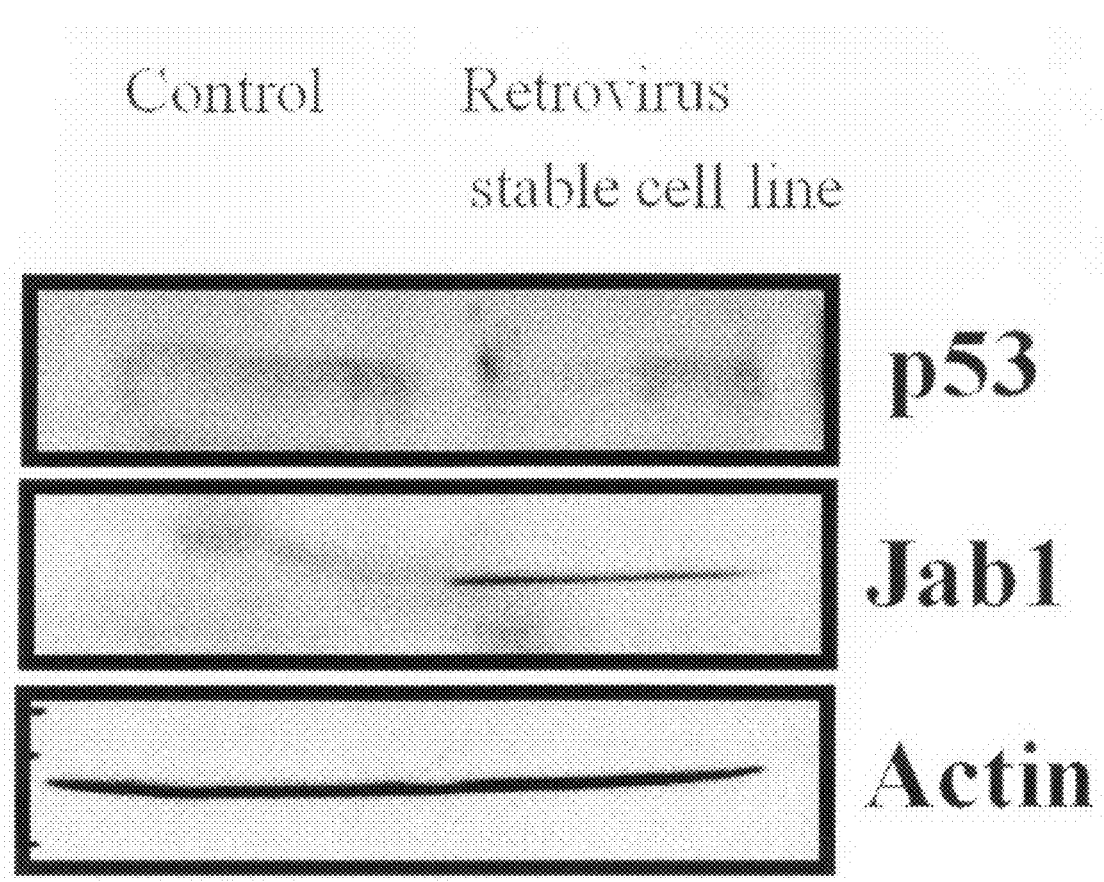
FIG. 18 shows the results of Western blotting, demonstrating that a NIH3T3 Jab1 retrovirus stable cell line is successfully established.

The decreased expression of p53, shown in FIG. 18, correlated with the results of Example 8. These results indicate that stable gene transfer using a recombinant retrovirus overexpressing Jab1 leads to degradation of a viral capsid protein.

INDUSTRIAL APPLICABILITY

As described hereinbefore, the present composition for treating a viral infection comprising Jab1 is capable of effectively treating diseases caused by flavivirus or pestivirus infections, including fever, rash, bleeding, jaundice, arthralgia, myalgia, encephalitis and meningitis.

DEPOSIT OF BIOLOGICAL MATERIAL

Deposit was made to the Korean Culture Center of Microorganisms (KCCM), 2nd Floor, Yulim Blid., 361-221, Hongje 1-dong, Seodaemun-gu, Seoul, 120-091, Korea on Aug. 34, 2004 (Assession No. KCCM 10592).

What is claimed is:

1. A method for treating a West Nile virus infection in a patient in need thereof, comprising administering a pharmaceutically effective amount of a Jun-activation binding protein 1(Jab1) having the amino acid sequence of SEQ ID No. 2 to the patient, wherein said Jab1 interacts with the capsid protein of West Nile virus (WNV-Cp) and stimulates degradation of the capsid protein thereby inhibiting WNV-Cp-induced apoptosis in a cell infected with West Nile virus.

2. The method as set forth in claim 1, wherein the Jab1 protein is encoded by the nucleotide sequence designated as SEQ ID No. 1.

3. The method as set forth in claim 1, wherein the infection is associated with fever, rash, bleeding, Jaundice, arthralgia, myalgia, encephalitis or meningitis.

* * * * *

SEQUENCE LISTING

```
<160> NUMBER OF SEQ ID NOS: 6

<210> SEQ ID NO 1
<211> LENGTH: 1262
<212> TYPE: DNA
<213> ORGANISM: Homo sapiens
<220> FEATURE:
<221> NAME/KEY: gene
<222> LOCATION: (1)..(1262)
<223> OTHER INFORMATION: Jab1
<220> FEATURE:
<221> NAME/KEY: CDS
<222> LOCATION: (94)..(1095)

<400> SEQUENCE: 1
ctggtgggga aggtccaaag cccgcacgct gaggcccagt agaagaaagt tgcatcttga      60
ttgtggagcg acagcttctc cggtgcctcg gcc          atg gca gct tcc ggg     108
                                              Met Ala Ala Ser Gly
                                              1               5 agt ggt atg gcc cag aaa acc tgg gaa ttg gcc aac aac atg cag gaa      156
Ser Gly Met Ala Gln Lys Thr Trp Glu Leu Ala Asn Asn Met Gln Glu
            10                  15                  20 gcg cag agt atc gat gaa atc tac aaa tat gac aaa aaa caa caa caa      204
Ala Gln Ser Ile Asp Glu Ile Tyr Lys Tyr Asp Lys Lys Gln Gln Gln
        25                  30                  35 gaa atc ctg gcg gcg aaa ccc tgg act aag gat cac cac tac ttt aaa      252
Glu Ile Leu Ala Ala Lys Pro Trp Thr Lys Asp His His Tyr Phe Lys
    40                  45                  50 tac tgc aaa atc tca gca ttg gct cta ctg aaa atg gtg atg cat gcc      300
Tyr Cys Lys Ile Ser Ala Leu Ala Leu Leu Lys Met Val Met His Ala
55                  60                  65 agg tca gga ggc aac ttg gaa gtg atg ggt ttg atg ctc ggg aaa gtc      348
Arg Ser Gly Gly Asn Leu Glu Val Met Gly Leu Met Leu Gly Lys Val
70                  75                  80                  85 gac ggc gag acc atg atc atc atg gac agt ttc gct ttg cct gta gag      396
Asp Gly Glu Thr Met Ile Ile Met Asp Ser Phe Ala Leu Pro Val Glu
                90                  95                 100 ggc aca gaa act cga gta aat gct caa gct gct gcg tat gag tat atg      444
Gly Thr Glu Thr Arg Val Asn Ala Gln Ala Ala Ala Tyr Glu Tyr Met
            105                 110                 115 gct gca tac ata gaa aat gcc aaa cag gtt ggc cgc ctt gag aat gca      492
```

```
      Ala Ala Tyr Ile Glu Asn Ala Lys Gln Val Gly Arg Leu Glu Asn Ala
                      120                 125                 130 atc ggt tgg tat cat agc cac cct ggt tat ggc tgc tgg ctc tcc ggg       540
Ile Gly Trp Tyr His Ser His Pro Gly Tyr Gly Cys Trp Leu Ser Gly
            135                 140                 145 att gat gtt agt aca cag atg ctg aac cag cag ttt caa gaa cca ttt       588
Ile Asp Val Ser Thr Gln Met Leu Asn Gln Gln Phe Gln Glu Pro Phe
150                 155                 160                 165 gta gca gtg gtg att gat cca acc aga aca atc tct gca gga aaa gtg       636
Val Ala Val Val Ile Asp Pro Thr Arg Thr Ile Ser Ala Gly Lys Val
                170                 175                 180 aat ctt ggc gcc ttt agg aca tat cca aag ggc tac aaa cct cct gat       684
Asn Leu Gly Ala Phe Arg Thr Tyr Pro Lys Gly Tyr Lys Pro Pro Asp
            185                 190                 195 gaa gga cct tct gag tac cag act atc cca ctt aat aaa ata gaa gat       732
Glu Gly Pro Ser Glu Tyr Gln Thr Ile Pro Leu Asn Lys Ile Glu Asp
        200                 205                 210 ttt ggc gtg cac tgc aaa caa tat tat gcc tta gaa gtc tca tat ttc       780
Phe Gly Val His Cys Lys Gln Tyr Tyr Ala Leu Glu Val Ser Tyr Phe
215                 220                 225 aaa tca tct ttg gat cgt aaa cta ctt gag ctt ttg tgg aat aaa tac       828
Lys Ser Ser Leu Asp Arg Lys Leu Leu Glu Leu Leu Trp Asn Lys Tyr
230                 235                 240                 245 tgg gtg aat acc ctg agt tcc tct agc ttg ctt act aat gca gac tac       876
Trp Val Asn Thr Leu Ser Ser Ser Ser Leu Leu Thr Asn Ala Asp Tyr
                250                 255                 260 acc aca ggc cag gtg ttt gat ttg tct gag aag tta gag cag tcg gaa       924
Thr Thr Gly Gln Val Phe Asp Leu Ser Glu Lys Leu Glu Gln Ser Glu
            265                 270                 275 gcc caa ctg gga cgt ggc agt ttc atg ttg ggc tta gaa aca cat gac       972
Ala Gln Leu Gly Arg Gly Ser Phe Met Leu Gly Leu Glu Thr His Asp
        280                 285                 290 cgc aag tcg gaa gac aaa ctt gcc aaa gct act aga gac agc tgt aaa      1020
Arg Lys Ser Glu Asp Lys Leu Ala Lys Ala Thr Arg Asp Ser Cys Lys
295                 300                 305 acc acc ata gaa gcc atc cat gga ctg atg tct cag gtt att aag gat      1068
Thr Thr Ile Glu Ala Ile His Gly Leu Met Ser Gln Val Ile Lys Asp
310                 315                 320                 325 aaa ctg ttt aat cag att aac gtt gct    tagtt accaccaagt acttctcaaa   1120
Lys Leu Phe Asn Gln Ile Asn Val Ala
                330 gctggtgtgt ggaaggaaaa gaagctcaag taacactttt aacccagtta ccaaaactca    1180 gattagaaga ctaaggtgct gtgtggtgtc ctgagtatta gcactgtaat aaaactatca    1240 cgtgaaaaaa aaaaaaaaaa aa                                             1262

<210> SEQ ID NO 2
<211> LENGTH: 334
<212> TYPE: PRT
<213> ORGANISM: Homo sapiens

<400> SEQUENCE: 2

Met Ala Ala Ser Gly Ser Gly Met Ala Gln Lys Thr Trp Glu Leu Ala
1               5                   10                  15

Asn Asn Met Gln Glu Ala Gln Ser Ile Asp Glu Ile Tyr Lys Tyr Asp
                20                  25                  30

Lys Lys Gln Gln Gln Glu Ile Leu Ala Ala Lys Pro Trp Thr Lys Asp
            35                  40                  45

His His Tyr Phe Lys Tyr Cys Lys Ile Ser Ala Leu Ala Leu Leu Lys
        50                  55                  60
```

Met Val Met His Ala Arg Ser Gly Gly Asn Leu Glu Val Met Gly Leu
 65                  70                  75                  80

Met Leu Gly Lys Val Asp Gly Glu Thr Met Ile Ile Met Asp Ser Phe
                 85                  90                  95

Ala Leu Pro Val Glu Gly Thr Glu Thr Arg Val Asn Ala Gln Ala Ala
            100                 105                 110

Ala Tyr Glu Tyr Met Ala Ala Tyr Ile Glu Asn Ala Lys Gln Val Gly
        115                 120                 125

Arg Leu Glu Asn Ala Ile Gly Trp Tyr His Ser His Pro Gly Tyr Gly
    130                 135                 140

Cys Trp Leu Ser Gly Ile Asp Val Ser Thr Gln Met Leu Asn Gln Gln
145                 150                 155                 160

Phe Gln Glu Pro Phe Val Ala Val Ile Asp Pro Thr Arg Thr Ile
                165                 170                 175

Ser Ala Gly Lys Val Asn Leu Gly Ala Phe Arg Thr Tyr Pro Lys Gly
            180                 185                 190

Tyr Lys Pro Pro Asp Glu Gly Pro Ser Glu Tyr Gln Thr Ile Pro Leu
        195                 200                 205

Asn Lys Ile Glu Asp Phe Gly Val His Cys Lys Gln Tyr Tyr Ala Leu
    210                 215                 220

Glu Val Ser Tyr Phe Lys Ser Ser Leu Asp Arg Lys Leu Leu Glu Leu
225                 230                 235                 240

Leu Trp Asn Lys Tyr Trp Val Asn Thr Leu Ser Ser Ser Leu Leu
                245                 250                 255

Thr Asn Ala Asp Tyr Thr Thr Gly Gln Val Phe Asp Leu Ser Glu Lys
            260                 265                 270

Leu Glu Gln Ser Glu Ala Gln Leu Gly Arg Gly Ser Phe Met Leu Gly
        275                 280                 285

Leu Glu Thr His Asp Arg Lys Ser Glu Asp Lys Leu Ala Lys Ala Thr
    290                 295                 300

Arg Asp Ser Cys Lys Thr Thr Ile Glu Ala Ile His Gly Leu Met Ser
305 310 315 320

Gln Val Ile Lys Asp Lys Leu Phe Asn Gln Ile Asn Val Ala
325 330

<210> SEQ ID NO 3
<211> LENGTH: 32
<212> TYPE: DNA
<213> ORGANISM: Artificial Sequence
<220> FEATURE:
<223> OTHER INFORMATION: primer for WNV-Cp amplification

<400> SEQUENCE: 3
ccggaattct ctaaaaaacc aggtggcccc gg 32

<210> SEQ ID NO 4
<211> LENGTH: 33
<212> TYPE: DNA
<213> ORGANISM: Artificial Sequence
<220> FEATURE:
<223> OTHER INFORMATION: primer for WNV-Cp amplification

<400> SEQUENCE: 4
gactagcggt cgcacccgcg catcgagctc gcc 33

<210> SEQ ID NO 5
<211> LENGTH: 32
<212> TYPE: DNA

```
<213> ORGANISM: Artificial Sequence
<220> FEATURE:
<223> OTHER INFORMATION: primer for DNA sequencing

<400> SEQUENCE: 5
ctattcgatg atgaagatac cccaccaaac cc                                32

<210> SEQ ID NO 6
<211> LENGTH: 33
<212> TYPE: DNA
<213> ORGANISM: Artificial Sequence
<220> FEATURE:
<223> OTHER INFORMATION: primer for DNA sequencing

<400> SEQUENCE: 6
tagcatctat gactttttgg ggcgttcaag tga                               33
```